(12) United States Patent
Foulkes

(10) Patent No.: US 11,357,616 B2
(45) Date of Patent: Jun. 14, 2022

(54) INTRAOCULAR CLIPPING DEVICE

(71) Applicant: Richard B. Foulkes, Lombard, IL (US)

(72) Inventor: Richard B. Foulkes, Lombard, IL (US)

( * ) Notice: Subject to any disclaimer, the term of this patent is extended or adjusted under 35 U.S.C. 154(b) by 0 days.

(21) Appl. No.: 17/018,042

(22) Filed: Sep. 11, 2020

(65) Prior Publication Data

US 2021/0077250 A1 Mar. 18, 2021

Related U.S. Application Data

(60) Provisional application No. 62/899,176, filed on Sep. 12, 2019.

(51) Int. Cl.
*A61F 2/16* (2006.01)
*A61F 9/007* (2006.01)

(52) U.S. Cl.
CPC ............. *A61F 2/16* (2013.01); *A61F 9/007* (2013.01); *A61F 2220/0008* (2013.01)

(58) Field of Classification Search
CPC ..... A61F 2/16; A61F 9/007; A61F 2220/0008
See application file for complete search history.

(56) References Cited

U.S. PATENT DOCUMENTS

| | | | | |
|---|---|---|---|---|
| 4,556,060 | A * | 12/1985 | Perlin | A61B 17/1227 24/552 |
| 10,426,479 | B2 | 10/2019 | Vold et al. | |
| 10,695,166 | B2 | 6/2020 | Willis et al. | |
| 2004/0006387 | A1* | 1/2004 | Kelman | A61F 2/1616 623/6.36 |
| 2005/0015143 | A1* | 1/2005 | Willis | A61F 2/1608 623/6.36 |
| 2012/0316644 | A1 | 12/2012 | Wald | |
| 2014/0276900 | A1* | 9/2014 | Cote | A61B 17/0231 606/107 |
| 2016/0022488 | A1 | 1/2016 | Dimmig et al. | |
| 2018/0185138 | A1* | 7/2018 | Ichikawa | A61F 2/16 |

FOREIGN PATENT DOCUMENTS

WO 2019155431 8/2019

OTHER PUBLICATIONS

Notification of Transmittal of the International Search Report and the Written Opinion of the International Searching Authority; International Application No. PCT/US 20/50373; dated Jan. 25, 2021; 16 pages.

* cited by examiner

*Primary Examiner* — Jennifer Dieterle
*Assistant Examiner* — Tiffany P Shipmon
(74) *Attorney, Agent, or Firm* — John H. Thomas, P.C.

(57) ABSTRACT

An intraocular clip comprises a flexible body connected to a plurality of fasteners. The fasteners, at least two of them, are configured on opposite sides of the body in an opposing relationship, and wherein the fasteners are biased to be engaging their respective opposing fasteners on the opposite sides of the body, however manipulation of the body moves the fasteners away from each other until the body is released and the fasteners bias toward each other. The fasteners have a proximal end joined to the body and a distal end on the opposite end of the fastener from the body. The distal ends of the fasteners comprise footpads, and the footpads on opposing fasteners engage each other when the fasteners are biased in their closed positions.

11 Claims, 22 Drawing Sheets

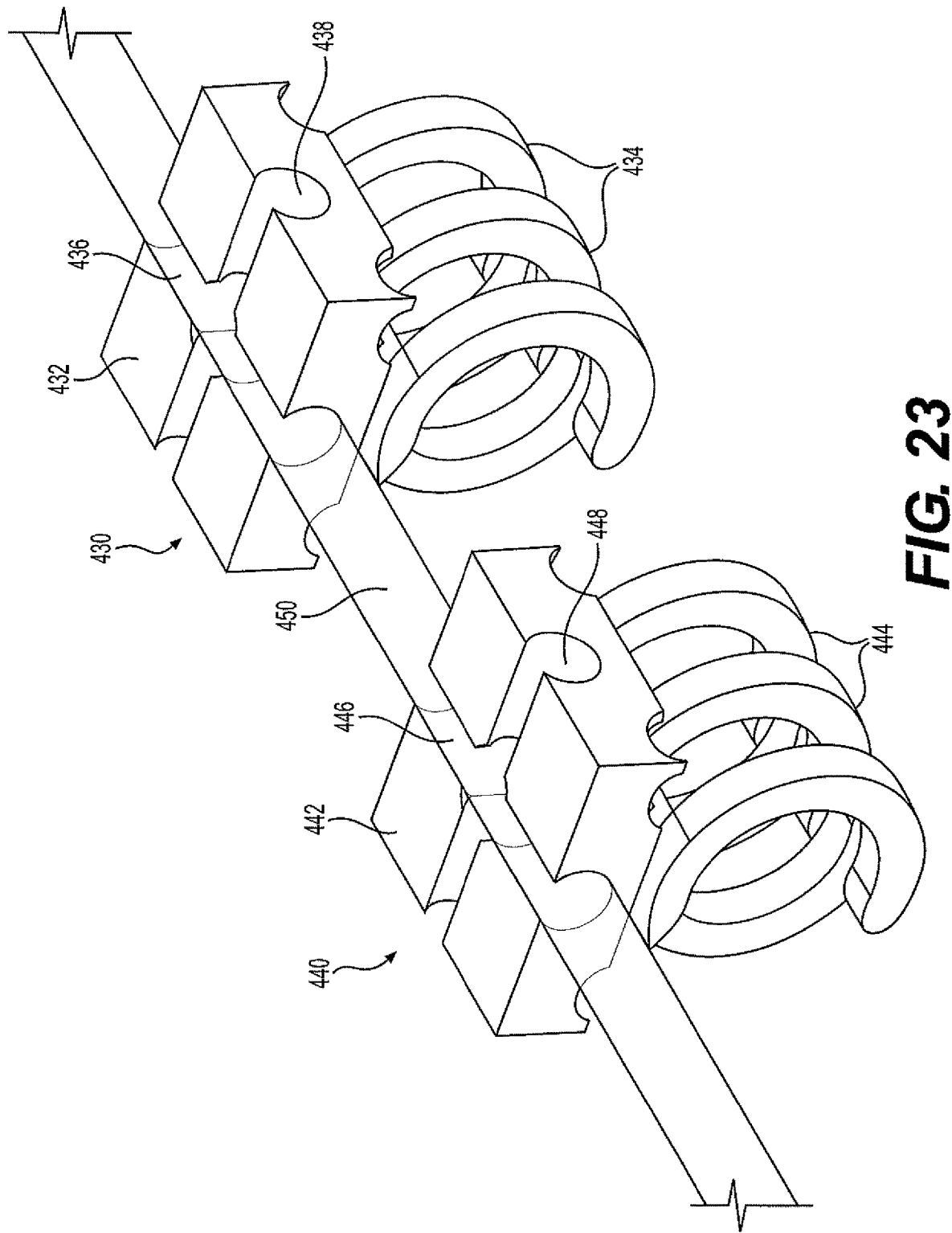

INTRAOCULAR CLIPPING DEVICE

The present application claims the benefit of filing of U.S. Provisional Patent Application No. 62/899,176 filed on Sep. 12, 2019, which is incorporated by reference herein in its entirety.

The present clipping device may be used inside the eye to close defects in the iris of an eye, attach intraocular lenses to the iris, and otherwise manipulate an iris in an eye temporarily during a procedure or permanently as a therapeutic tool. Special efficacy is believed with respect to management and treatment of an iris.

BACKGROUND

The human iris is a complex pigmented tissue which provides multiple functions to vision and eye health. It is part of the anterior segment of an eye which allows for light to be directed through the central lens, and it regulates light levels to the retina. The aperture effect or numerical aperture also improves vision by giving depth of focus. Any defect in the iris will lead to a patient experiencing glare, secondary images and loss of best corrected vision. A common reason for iris defects is iris extrusion during cataract surgery. The pigment can be scraped off in a minor case and a hole or total loss will be seen in more extreme cases. Trauma can lead to complex areas of loss or distortion. Congenital defects are also common and range from sectional loss in coloboma to full loss in aniridia.

Currently, the method for correcting these defects typically involves the use of a suturing technique. Two to three small incisions are made in the cornea. A long needle is passed through an incision passing through one side of the defect proceeding through the far side of the defect. The needle tip is then inserted into a cannula or a syringe needle and then pulled out of the eye. Currently two methods of tying of the suture are described. The suture can be drawn out of a third incision on both sides and knots are thrown and pulled into the eye. The "slip" knot is favored. To close a larger defect this process is repeated several times to provide an adequate closure. A more recent technique is called the "4 throw". This is accomplished with only two incisions. The above steps are followed. The suture is pulled beyond the incision out of the second incision and the suture is passed four times though the loop and is then slid back into the eye. This "noose" is said to hold well but its long term has not been tested. To close a pupil a series of sutures can be woven through the edge and then drawn up to "cinch" the area needing closure.

Recently a method for suturing an intraocular lens (IOL) to the back of the iris has been described. The IOL is held behind the iris and a suture is passed though and behind the arm or "haptic" of the IOL, and it is then tied down. This allows an IOL to be placed when the capsular structure is missing. An IOL known as the Artisan or Wurst lens was introduced in the 1980s for clipping onto the iris with two "claw" like plastic clips. These have done well and show that the iris can tolerate clipped devices for decades without harm.

Though generally effective, these steps repair or prevent iris defects are presented to highlight time consuming difficulty that require two to three openings and needle penetration of the iris. Though reversible, it is not a technique that lends itself to temporary securing of the iris as might be considered in a floppy iris syndrome where risk of the iris sweeping out of the primary incision is high. Another technique that is currently employed for suture of the iris is recreating a round pupil. In these cases, trauma or surgical issues have led to a permanently dilated pupil. This leads to aberration, glare and light sensitivity as well as poor cosmetic appearance. Generally, the same technique is employed only to create closure and the angles require at least four to six openings to pass needles in the circumferential fashion needed to create a round effect. Though the problem can be addressed, it can be complicated if the patient requires retinal surgery in the future. As retinal surgery requires accessing the posterior retina, these sutures would need to be taken down in order to open the pupil which then requires another extensive surgery to resuture the iris again if no further retinal care were anticipated.

In modern cataract surgery, a lens is removed from within a lens capsule that is attached to the ciliary body by tiny strands known as zonules. On completion of cataract removal, the capsular "bag" becomes the support for an intraocular lens. If the capsular bag is lost due to weakness of the zonules, trauma, or from other problems that have made the capsule insecure for IOL placement, the surgeon has two current lens options. An FDA approved anterior chamber implant can be placed, residing on top or the iris and fixating into the iris corneal angle. These lenses can do well but often lead to pain, chronic inflammation, elevated eye pressure and corneal failure from loss of the inner lining endothelial cells. Because of these issues, novel techniques have been developed for placing a three-piece IOL posteriorly. These techniques are challenging and they leave a vulnerable lens arm or haptic lodged into the sclera in two locations. Because these sutures are externalized, there is a lifetime risk that they can introduce infection into the eye or that they can give way or erode back into the eye. The long-term effects regarding these techniques are not known and they are not in common use by average surgeons. An alternate method is to suture the three-piece IOL onto the iris as suggested above. This is done using the described methods passing the suture through the iris under the IOL haptic then out of the iris and then out or the eye to tie the knot. This can only be applied to a three-piece IOL which limits choice, and it is secured in one spot, as the technique is time consuming and requires puncturing the iris. Iris movement from the single attachment may lead to rubbing against the iris and pigment loss, elevated eye pressure and inflammation.

SUMMARY

The present novel invention addresses all of these problems and more with a quick and easy to use tool. It can be used to close iris defects and pupil issues quickly and through a single incision. They can be quickly and easily reversed when needed and could easily be used for even a temporary closure in the case of floppy iris syndrome. The iris could be "pinned" open and then reversed at the end of the procedure. In the case of iris trauma, a perfect aperture could be created and if needed, quickly taken down for retinal surgery and then reclosed at the conclusion. This method allows for capturing the arm of an IOL placed behind the iris and with several connectors attaching to any IOL, including astigmatic or other premium IOLs. These connectors could "space" the lens behind the iris by adding an attachment to the arm of the IOL which is then secured onto the iris. As the attachments can be left and then easily retrieved, this method is a way to place an intraocular device into the anterior or posterior chamber for drug delivery or other applications. For broader defects or large defects, the tool could be used to secure an iris replica without angle fixation. It could provide an attachment for monitoring tools, cameras and cosmetic appearance. An iris stimulator could be clipped strategically to overcome neurotropic paralysis of the constricting portion of the iris. In cataract surgery a common complication is a tear in the posterior capsule. These tears cause the vitreous to come forward and the posterior placement of the IOL becomes impossible. The capsule could be grasped and clipped closed using the method described for the device. The IOL could also be clipped to the anterior capsule to allow it to be placed in its normal space and to allow the use of a one-piece IOL. This could be further facilitated by a clipping attachment onto the arm of the IOL. By linking several clips, the iris could be drawn together or pushed open. A nano pump system could drive a small bladder clipped near the pupil and could open and close a tonic non mobile pupil.

In one example, an intraocular clip comprises a flexible body connected to a plurality of fasteners. The fasteners, at least two of them, are configured on opposite sides of the body in an opposing relationship, and wherein the fasteners are biased to be engaging their respective opposing fasteners on the opposite sides of the body, however manipulation of the body moves the fasteners away from each other until the body is released and the fasteners bias toward each other. The fasteners have a proximal end joined to the body and a distal end on the opposite end of the fastener from the body. The distal ends of the fasteners comprise footpads, and the footpads on opposing fasteners engage each other when the fasteners are biased in their closed positions. The flexible body and plurality of fasteners may be a single unitary piece. The fasteners may be a plurality of opposing comb extensions. The clip may define a length, and the length of the clip is between 0.5 and 5 mm, or alternatively, between 1 and 2 mm. The footpads may have a flat face or a textured face or a pointed face. The clip may further comprise a spring attached to the body to bias the body to urge the fasteners together in a closed position.

In another alternative, an intraocular surgical procedure comprises the steps of providing a plurality of intraocular clips comprising a flexible body connected to a plurality of fasteners. The fasteners are configured on opposite sides of the body in an opposing relationship, and wherein the fasteners are biased to be engaging their respective opposing fasteners on the opposite sides of the body, however manipulation of the body moves the fasters away from each other until the body is released and the fasteners bias toward each other. The fasteners may have a proximal end joined to the body and a distal end on the opposite end of the fastener from the body, and the distal ends of the fasteners comprise footpads, and the footpads on opposing fasteners engage each other when the fasteners are biased in their closed positions. The method further includes providing a ring having a predetermined diameter, using the clip, securing the iris to the ring to thereby secure the iris in a predetermined diameter.

In another example, an intraocular surgical procedure comprises the steps of providing a plurality of intraocular clips comprising a flexible body connected to a plurality of fasteners, wherein the fasteners are configured on opposite sides of the body in an opposing relationship, and wherein the fasteners are biased to be engaging their respective opposing fasteners on the opposite sides of the body, however manipulation of the body moves the fasters away from each other until the body is released and the fasteners bias toward each other. The fasteners have a proximal end joined to the body and a distal end on the opposite end of the fastener from the body, and the distal ends of the fasteners comprise footpads, and the footpads on opposing fasteners engage each other when the fasteners are biased in their closed positions. The procedure further comprises locating the adjacent edges of a gap in a patient iris, and drawing adjacent edges of the gap together with the fasteners of the clip whereby the gap in the iris is closed.

A still further example includes an intraocular surgical procedure comprising the steps of providing a plurality of intraocular clips comprising a flexible body connected to a plurality of fasteners. The fasteners are configured on opposite sides of the body in an opposing relationship, and wherein the fasteners are biased to be engaging their respective opposing fasteners on the opposite sides of the body, however manipulation of the body moves the fasters away from each other until the body is released and the fasteners bias toward each other. The fasteners have a proximal end joined to the body and a distal end on the opposite end of the fastener from the body, and the distal ends of the fasteners comprise footpads, and the footpads on opposing fasteners engage each other when the fasteners are biased in their closed positions. The procedure further includes providing an intraocular lens for insertion in a patient's eye, positioning the intraocular lens in the capsule of a patient's eye, and using the clip, attaching an edge of the intraocular lens to the patient iris to secure the lens in place.

BRIEF DESCRIPTION OF THE DRAWINGS

FIG. 23 is a perspective view of alternative examples of iris clips as described herein.

DETAILED DESCRIPTION

Intraocular iris clips do not currently exist for the utility of rapid closure and alteration of the iris tissue for temporary or permanent manipulation of this vital visual anatomic tissue. A biocompatible device for clipping onto the iris strands allows for many useful maneuvers to improve the safety during intraocular surgery. The essential tool is a ring of pliable material like polyamide. The material could alternatively be made of polysaccharide that would be absorbable or non-magnetic pliable metals that are biocompatible. The fasteners may be composed of inert materials like polymers, silicone, acrylic, non-magnetic metals and elastics as well as absorbable materials like polysaccharide gels or collagen. On the opening part of this device is a flat footpad, also referred to herein as a foot plate, that can be smooth, roughened or comb like to grasp the iris strands. The configuration of the foot plates will vary by the task involved. To close a radial opening the footpads/foot plates would be elongated like the strands they are capturing to allow for a zone to be captured and closed with minimal tension or damage to the tissue. These may be of variable length depending on the size of the defect to be closed. If there is a paucity of tissue, the arch itself may be placed in a radial fashion over the defect. A wider clip may therefore be used to cover a zone where the tissue itself will not be able to be stretched over the defect. Clips may be placed on either side of a large defect and a bridging piece then attached to the clips to cover the zone. The power unit or spring of the device is a curved material that can include a central zone for inserting a stiffening device to increase the spring power of the closure. The clip can be approached vertically, and it is gripped by overhanging elements. A central groove may be a part of the clip to act as a stabilizing element when the device is bent up to open the jaws of the various iterations. A V-shaped groove may be configured in the clip to insert a spring like device made of material that resists bending and will add spring power to the closure. The shape is standardized to all of the various closure iterations so that the device used to place the clip can be used in most applications.

Figure 1:
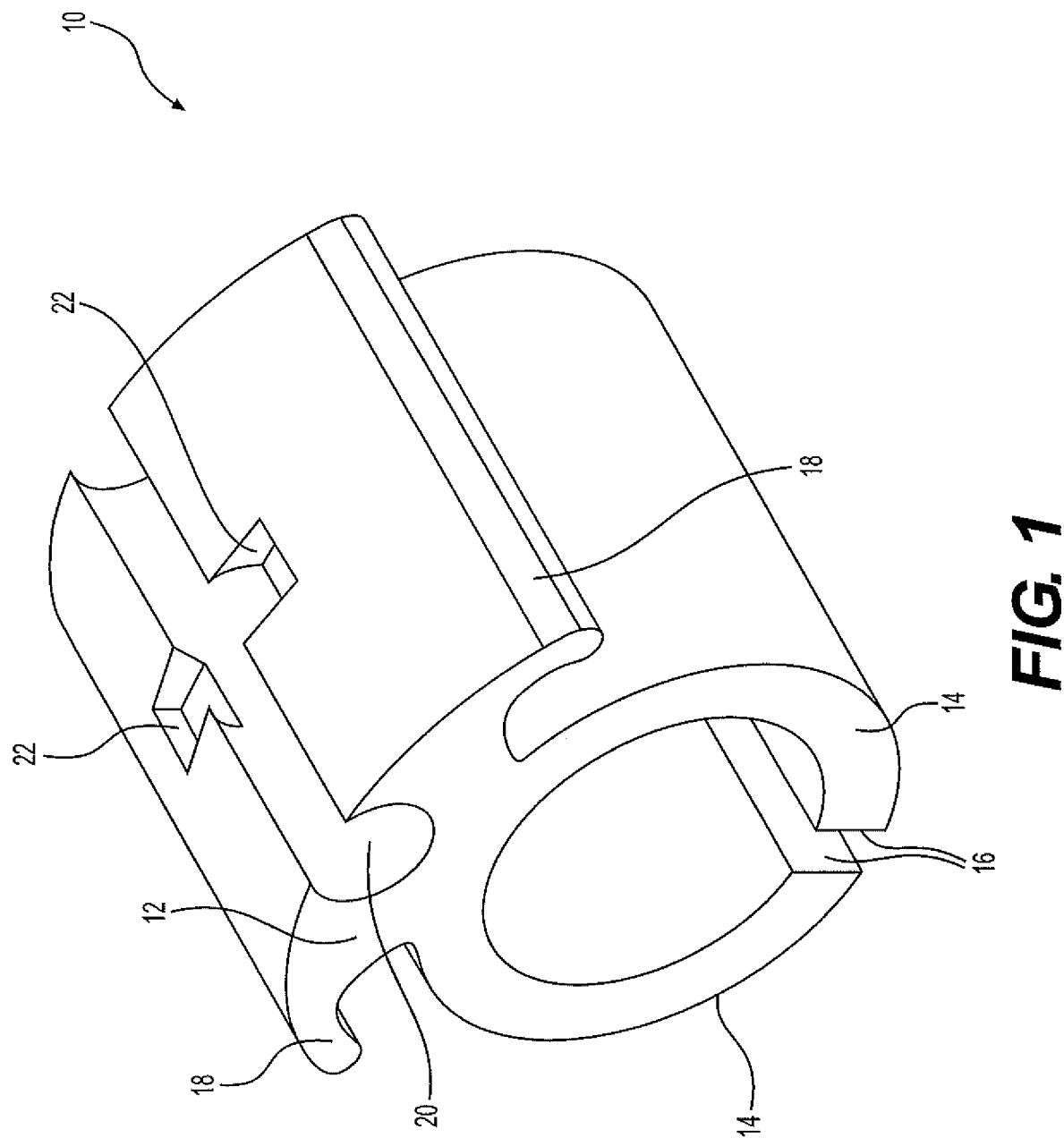
FIG. 1 is a perspective view of one example of an iris clip as described herein.

FIG. 1 illustrates a basic example of a clip 10 that includes a flexible body 12 and a pair of fasteners 14 that are integrally connected to the flexible body. At the distal ends of the fasteners 14 are footpads/foot plates 16 that engage each other or at least biased toward each other when the clip 10 is its closed position as shown. The flexible body 12 may be flexed so that the fasteners 14 are closed and biased shut or otherwise flexed apart when the flexible body is pinched or flexed to pull apart the fasteners. In this example clip 10, the flexible body 12 includes a pair of wings 18 on opposite sides and a central channel 20. As shown in other drawings, an insertion and removal device includes three rods that are positioned under each wing and in the channel respectively. By bearing down on the channel 20 and retaining the wings 18 in place, the fasteners 14 can be opened or closed by the up and down movement of the rod in the channel, or alternatively by the up and down movement of the outside rods with the central rod held stable.

Figure 2:
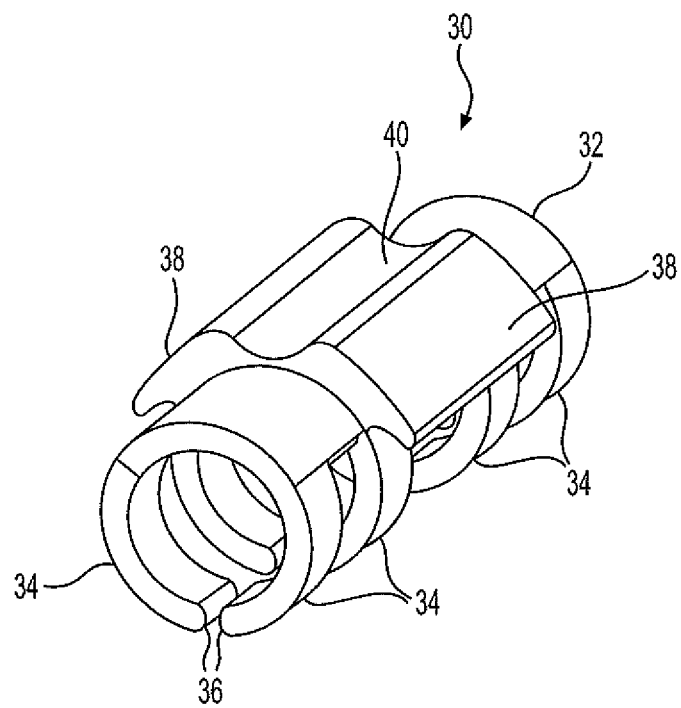
FIG. 2 is a perspective view of a second example of an iris clip as described herein.

FIG. 2 illustrates a second, longitudinally longer version of an iris clip 30. The clip 30, like clip 10, has a round longitudinal cross-section. The flexible body 32 connects opposing fasteners 34 on each side of the flexible body 32. While FIG. 1 had fasteners 14 that were a continuous surface on each side, the fasteners 34 in FIG. 2 illustrate four separate arms that are comb-like features that are shown in opposite, opposing positions with foot pads 36 that meet and engage each other when in the biased closed position shown. The flexible body 32 has wings 38 that are a part of the flexible body. There is also a top channel 40 that extends longitudinally on the top of the flexible body 32. The operational mechanism of opening and closing the fasteners 34 is as briefly described in FIG. 1 and as will be shown later herein.

Figure 3:
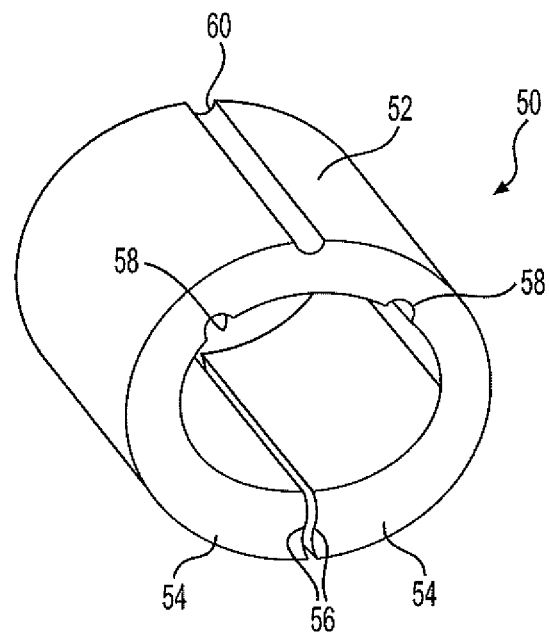
FIG. 3 is a perspective view of a third example of an iris clip as described herein.

FIG. 3 is a still further alternative example of an iris clip 50. The clip 50 includes a flexible body 52 and fasteners 54 that have foot pads 56 on the distal end of the fasteners. The flexible body 52 has two inside channels 58 that run longitudinally along the flexible body and are on the bottom or inside of the clip 50. A third channel 60 runs longitudinally along the top and middle of the flexible body 52. The clip 50 is shown in its biased closed positioned where the foot pads 56 are touching or adjacent each other. In operation, a three-pronged tool will have its three prongs or rods positioned in the underneath channels 58 and top channel 60. By a user pressing down on the top channel 60 while also holding the bottom channels 58 stationary, or vice versa moving the side prongs/rods up and down and keeping the center rod/prong stationary, the fasteners 54 are biased open.

Figure 4:
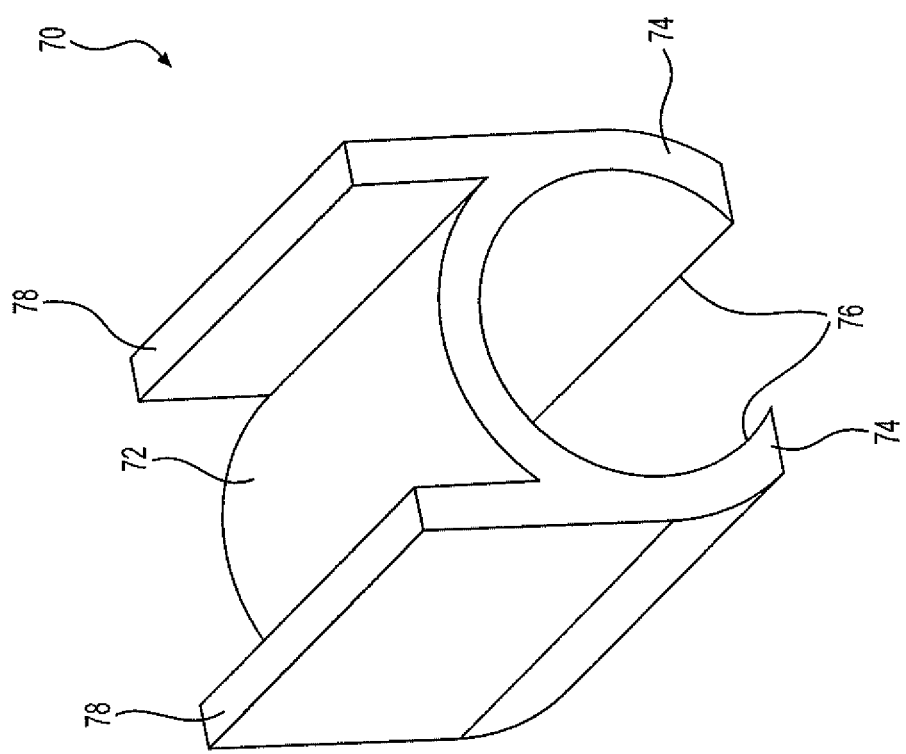
FIG. 4 is a perspective view of a fourth example of an iris clip as described herein.

FIG. 4 illustrates a still further example of an iris clip 70. This clip 70 has a flexible body 72 and opposite fasteners 74. On the distal end of the fasteners 74 are foot pads 76. In this example, the foot pads 76 are a pointed edge along the distal, longitudinal length of the fasteners 74. Wings 78 are shown extending upwardly from the flexible body 72, and the clip 70 is shown in the partially open position where the foot pads 76 are not adjacent or touching each other. This clip 70 is moved to an open position as shown by manually squeezing together the wings 78. The clip 70 may be moved to a closed position by simply releasing the wings 78 wherein the fasteners 74 will come together to their biased closed position.

Figure 5:
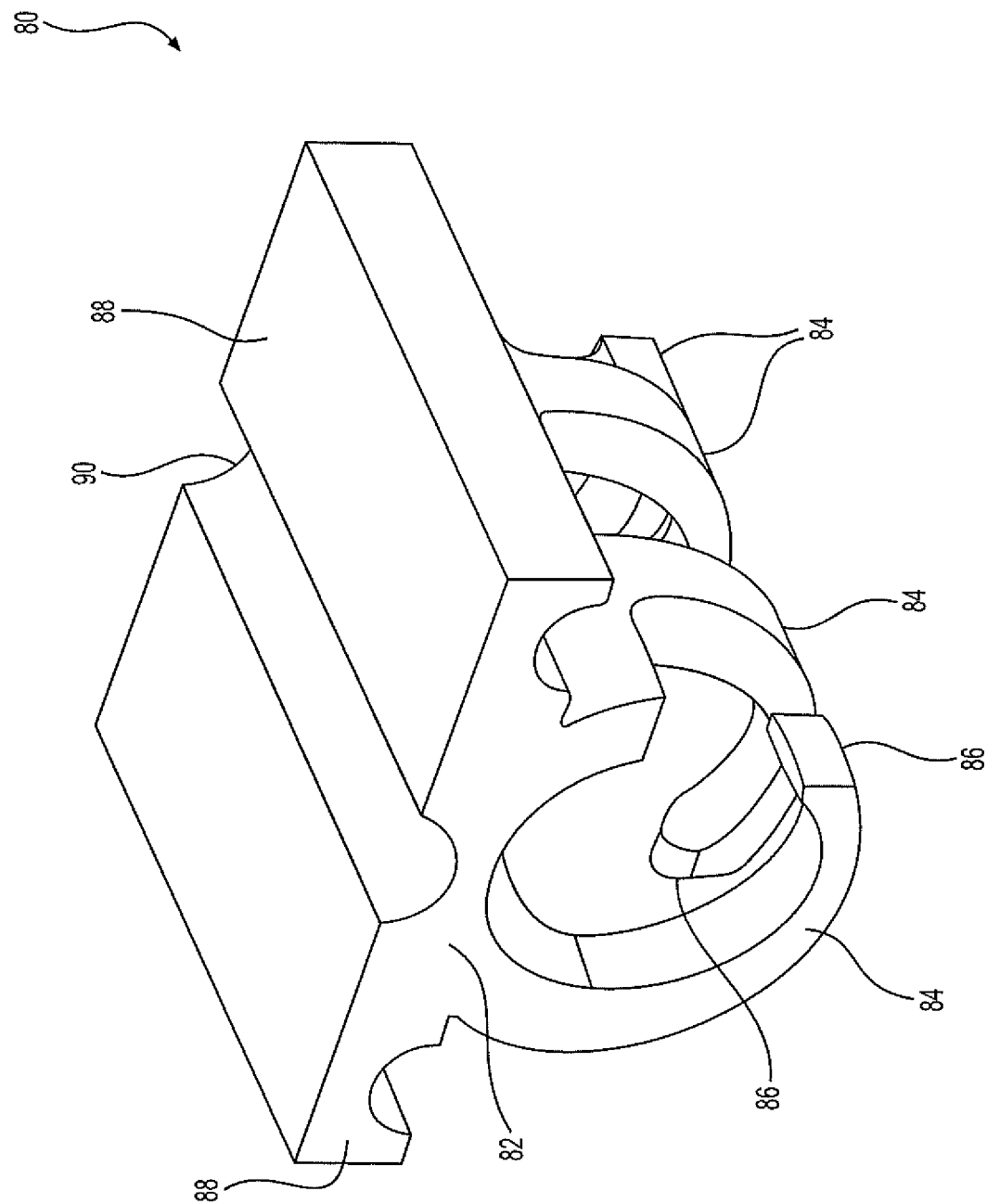
FIG. 5 is a perspective view of a fifth example of an iris clip as described herein.

FIG. 5 is an illustration of a still further example of an iris clip 80. The iris clip 80 has a flexible body 82 and fasteners 84. The fasteners 84 are comb-like fingers. The distal end of each fastener 84 has a rounded but pointed foot pad 86. The clip 80 is shown in its biased closed position. The flexible body has wings 88 and a central top channel 90 along its longitudinal length. This clip 80 would be opened and closed using the same or similar three-pronged tool as described earlier and also later herein. In this example, clip 80 has fasteners 84 that are overlapping fingers so that the foot pads 86 on the distal end of the fasteners overlap, and the foot pads do not engage the opposite foot pads. This example clip 80 might be used in connection with the joinder of fibrous tissue that the fasteners 84 might intertwine with. Other uses are of course possible.

Figure 6:
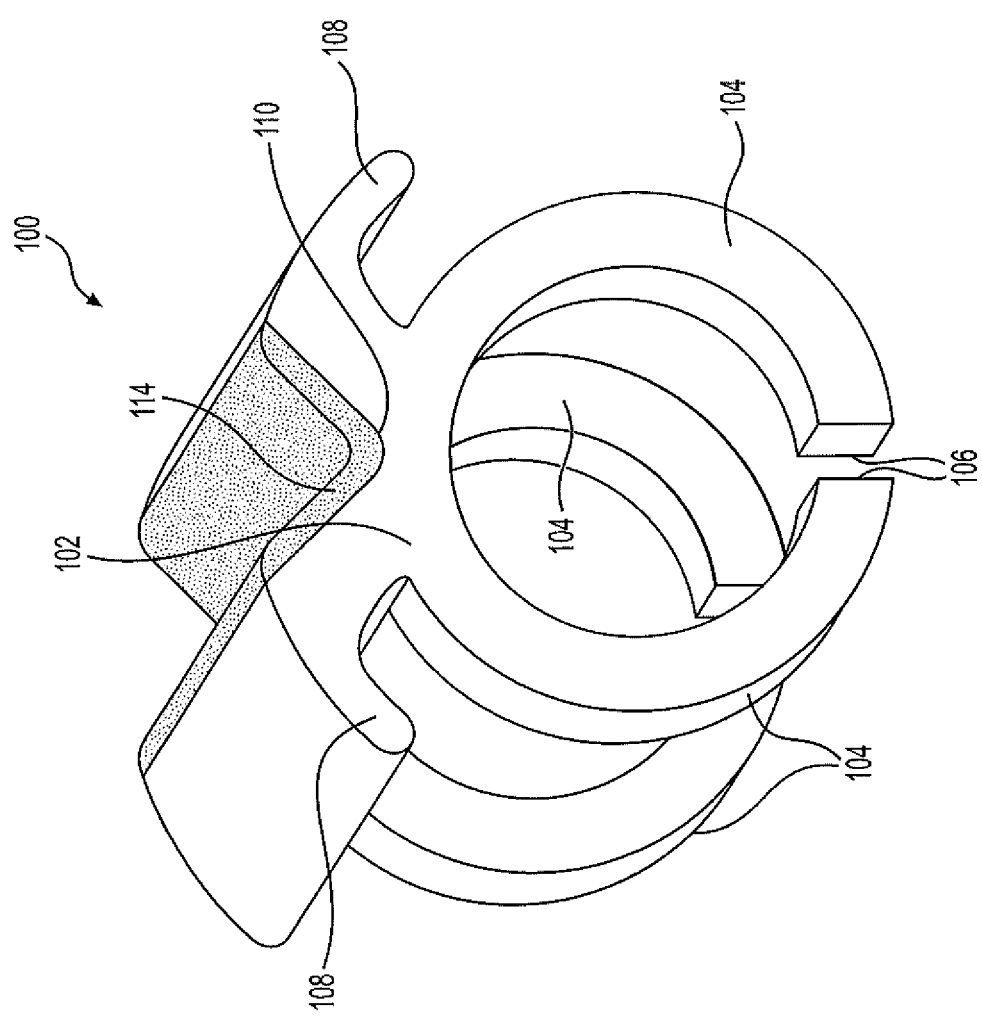
FIG. 6 is a perspective view of an example of an iris clip as described herein with a stiffening element grafted thereon.

As explained earlier herein, the clipping strength of a given clip will depend on the flexibility of the flexible body that holds or is integral with the fasteners. The clip may be formed of multiple alternative materials and combinations of materials and thicknesses of materials to achieve a desired clipping strength. One example of how this may be engineered is shown in FIG. 6. FIG. 6 illustrates an iris clip 100 with a flexible body 102 and fasteners 104. The fasteners have foot pads 106 on their distal ends. In this example, the fasteners 104 are opposing arms, like a comb, that have foot pads 106 that meet each other when the clip 100 is in its biased closed position. The flexible body 102 includes wings 108 and a central, longitudinal channel 110 on its top. In this example, however, a spring member 114 is integrally fused in the central channel 110. The integral spring 114 provides supplemental stiffening and closure strength to bias and bring together the fasteners 104.

Figure 7:
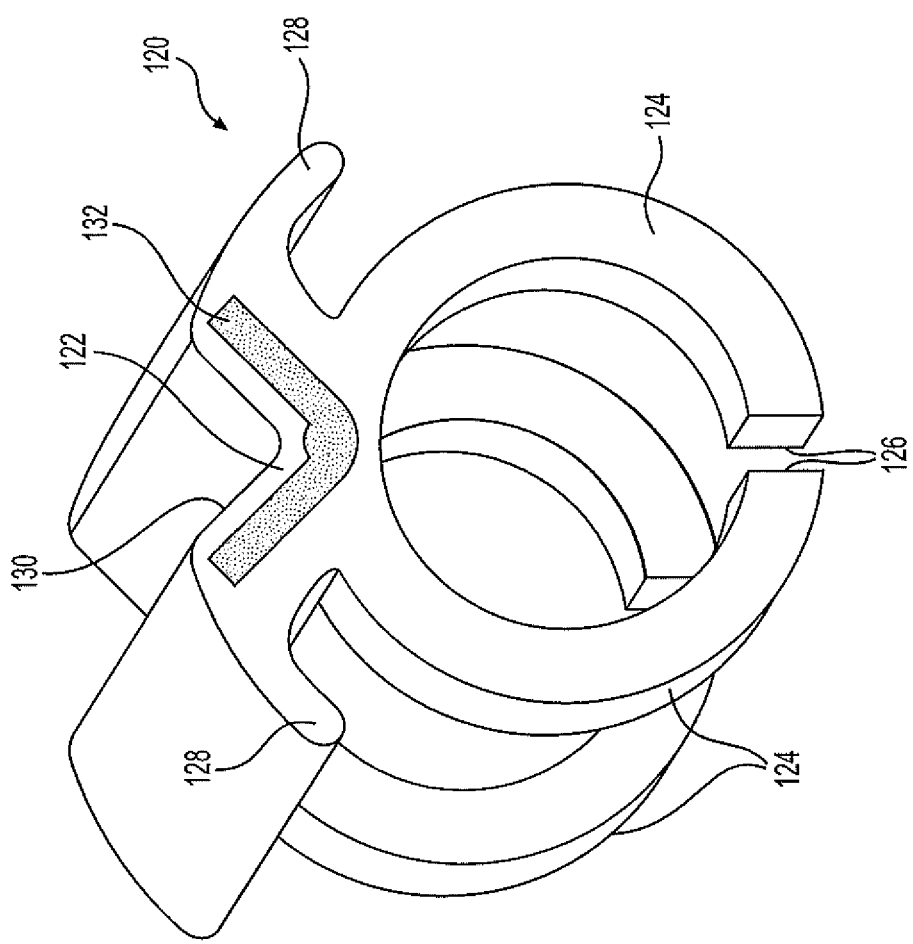
FIG. 7 is a perspective view of an example of an iris clip as described herein with a stiffening element inserted therein.
Figure 8:
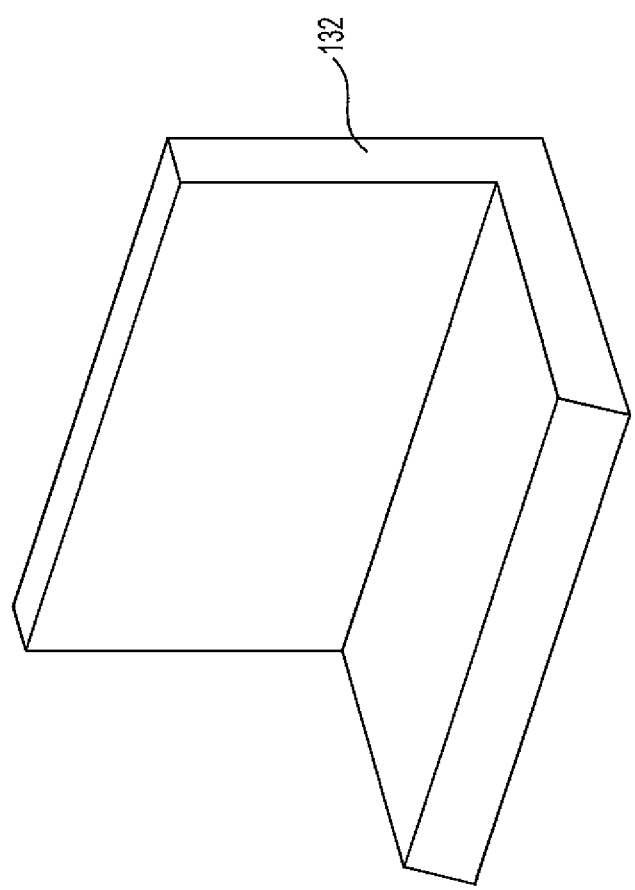
FIG. 8 is a perspective view of an example of a stiffening element.

In FIG. 7, an iris clip 120 includes a flexible body 122 and fasteners 124. The distal ends of the fasteners 124 have foot pads 126 that meet each other. In this example, the fasteners 124 are comb-like fingers where the opposing footpads meet each other. The flexible body 122 includes wings 128 and a central top channel 130 that facilitate opening and closing as explained herein. Positioned inside the longitudinal middle of the flexible body 122 is a spring 132 that provides extra stiffening and strength to the clip 120. FIG. 8 illustrates the spring 132 alone when out of the clip 120. This spring 132 may be especially chosen for its stiffness so that the clip has a desired, predetermined closing power.

Figure 9:
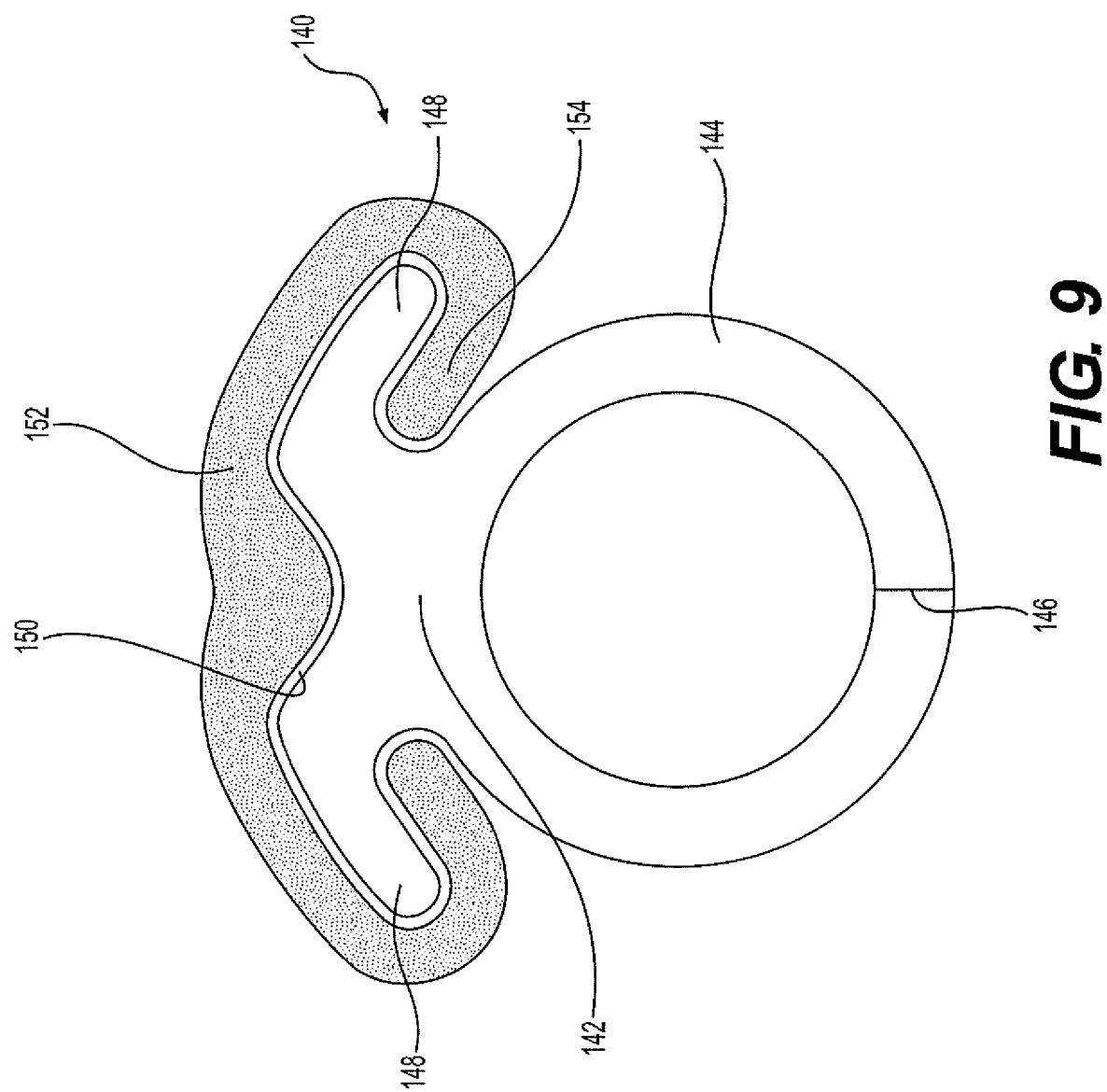
FIG. 9 is a perspective view of an example of an iris clip with a secondary clip placed over the iris clip.

FIG. 9 is an illustration of an iris clip that has a flexible body 142 and fasteners 144 with foot pads 146. The flexible body 142 includes wings 148 and a central longitudinal channel 150. In this example of a clip 140, there is a secondary clip 152 that includes arms 154 that wrap around and engage the flexible body 142. This secondary clip can be selected and used to increase or reduce the closing power of the clip 140 but pressing the fasteners 144 together or apart by their respective pushing or pulling on the wings 148 and channel 150.

Figure 10:
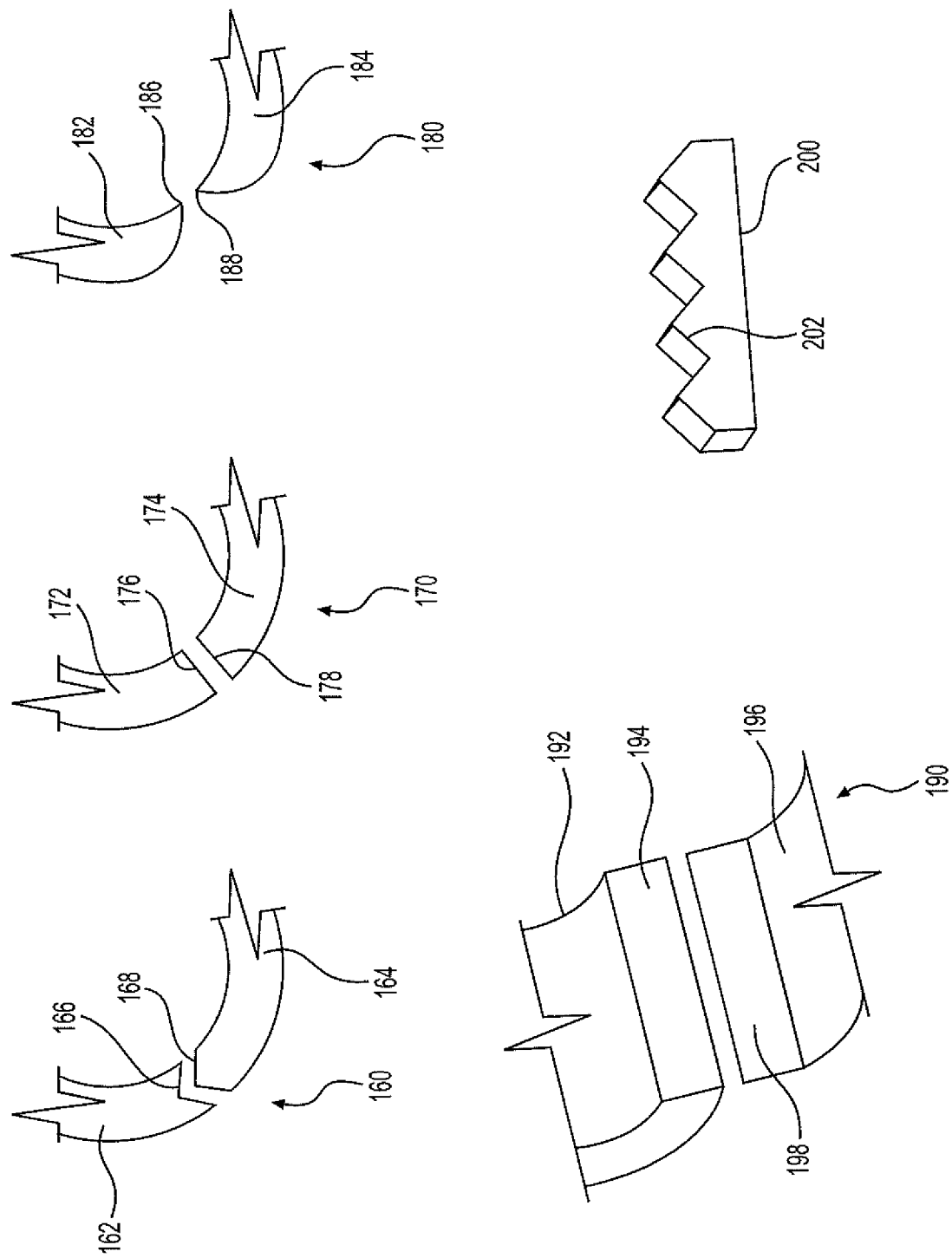
FIG. 10 is a collection of perspective views of examples of footpad shape alternatives.

The footpads of the various iris clips may take multiple alternative forms and shapes. The footpads in FIGS. 1-9 are examples of some shapes. FIG. 10 illustrates additional shapes. Each of the examples of FIG. 10 illustrate the footpad portions only of the various clips. Clip 160 displays opposing fasteners 162 and 164. Fastener 162 has a female v-shape footpad 166. Fastener 164 has a male v-shape footpad 168. The respective footpads 166 and 168 interact to close and secure the fasteners 162 and 164 together. Clip 170 includes fasteners 172 and 174. Their respective footpads 176 and 178 are each flat and will engage each other along their flat faces. Clip 180 has fasteners 182 and 184 that each have pointed footpads 186 and 188 respectively. Clip 190 has opposing fasteners 192 and 196 and solid footpads 194 and 198 respectively that engage when the clip is in its biased closed position. An alternative surface is shown that has some texture. The footpad surface 200 has a textured, toothed surface 202 that may engage an opposing fastener footpad surface.

The fasteners may have many shapes and may be designed to conform with the function that they are being inserted to perform. Examples include FIGS. 1, 3 and 4 that have solid, continuous one-piece fasteners, while FIGS. 2, 5, 6 and 7 illustrate various alternative comb-like shapes for their fasteners. Of course other fastener shapes and combinations of shapes are possible.

Figure 11:
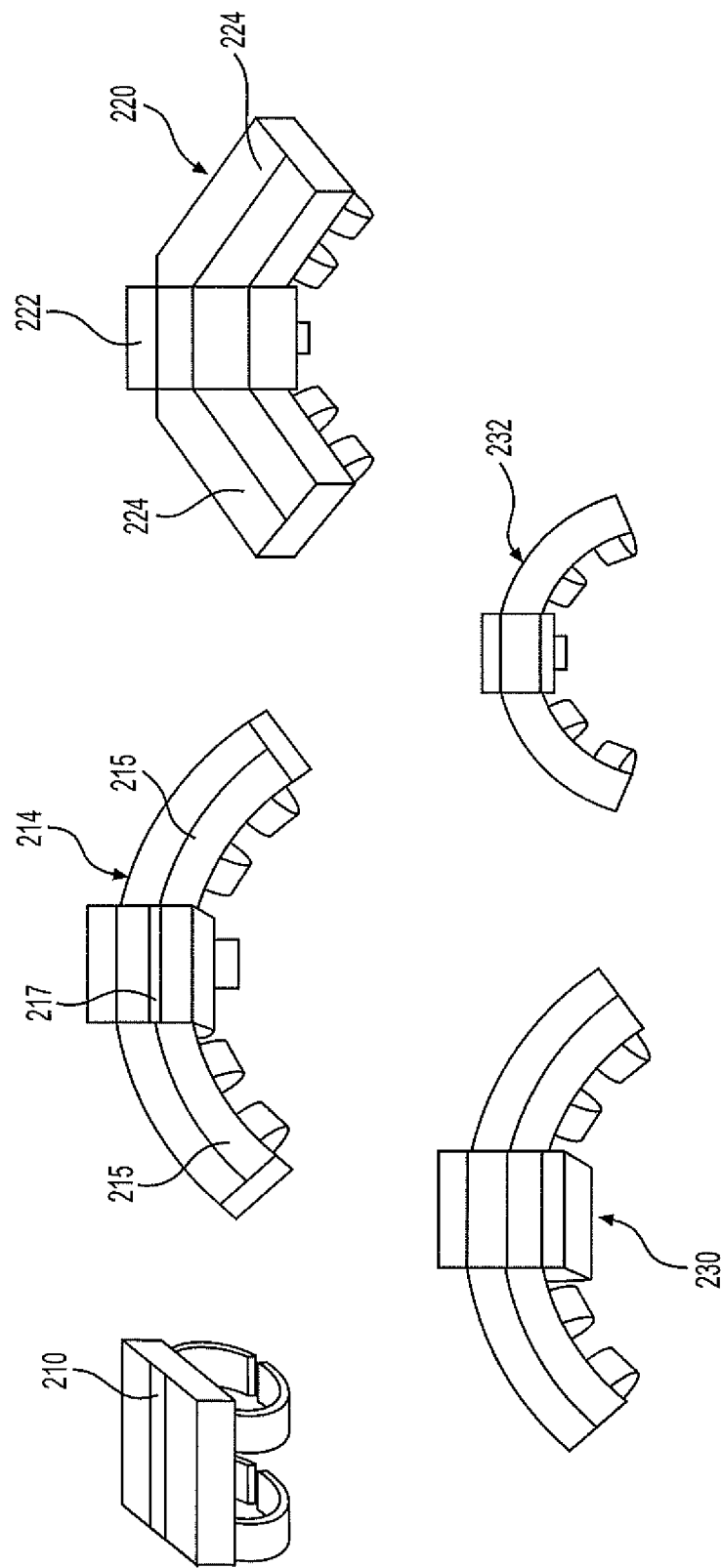
FIG. 11 is a collection of perspective views of examples of iris clips having different shapes and sizes.

The iris clips described herein may come in various shapes and sizes. In FIG. 11, several examples of the qualitative shapes are seen. Clip 210 has a standard rectangular flexible body shape in top view. Clip 214 has a rectangular flexible body 217 centerpiece with two curved extensions 215 on each side of the centerpiece. Clip 220 has a chevron shape with a rectangular centerpiece 222 and angled extensions 224. And clips 230 and 232 are arched and reverse-arched clips. In this iteration the closure elements are curved vertically up or down and could be useful in attaching curved objects within the eye such as a lens or gather iris tissue in an arch around a pupil that requires opening.

Figure 12:
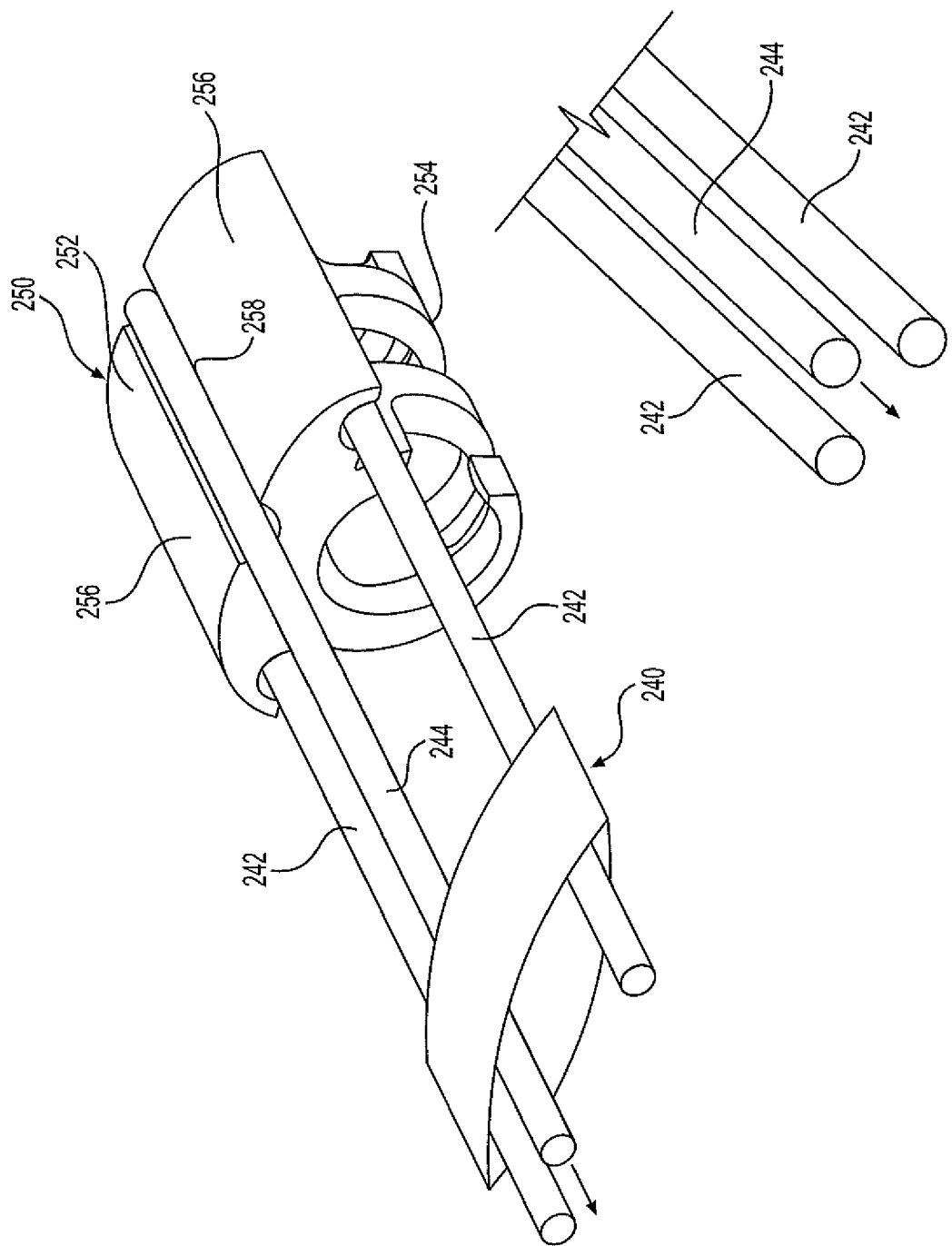
FIG. 12 is a perspective view of an insertion device and how it operates with an iris clip.
Figure 13:
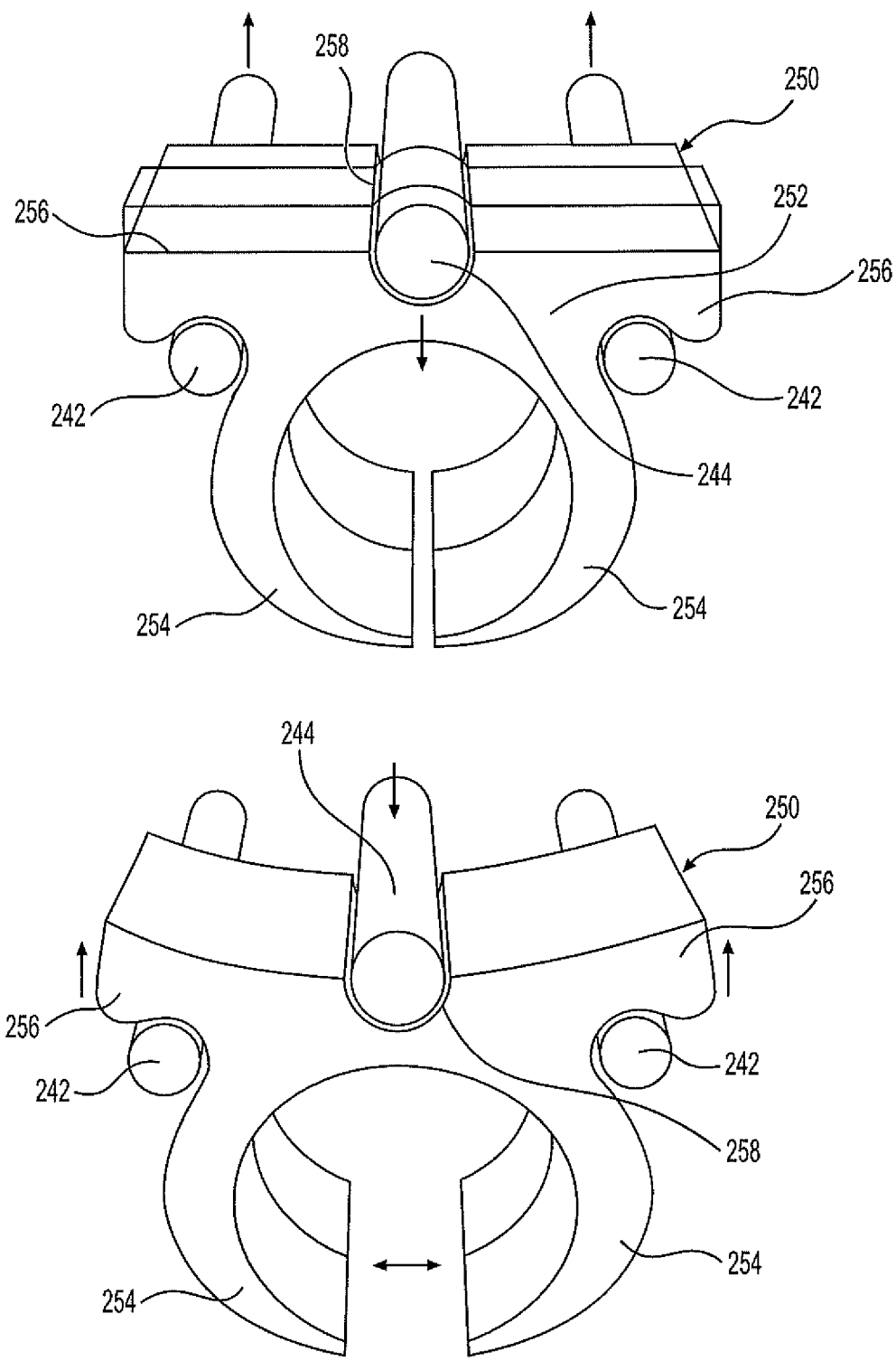
FIG. 13 is a perspective view of an insertion device and how it operates with an iris clip.

FIGS. 12 and 13 illustrate an insertion tool and its use in spreading and installing an iris clip. In FIG. 12, the insertion tool 240 includes three rods—two side rods 242 and a center rod 244. Iris clip 250 has a flexible body 252 and fasteners 254. The flexible body includes wings 256. The side rods 242 are placed under each side wing 256 with the center rod 244 placed in the top channel 258. By then applying a downward force to the center rod 244 while the side bars 242 are moved upwardly or held stationary, the wings raise up and the fasteners spread open. FIG. 13 illustrates the same iris clip 250 and the three insertion rods 242 and 244. The fasteners 254 are shown in the biased closed position on top and the spread open position on the bottom based on the interaction of movement of the rods 242 and 244.

Clips may be fashioned to enable the attachment of iris replicas. These would allow for simple clipping of an iris replica to the iris clips which are secured onto the natural iris strands present in a patient eye. The same technique would allow for intraocular devices like drug delivery systems to reside on the iris. An intraocular pressure monitor or video camera could be attached easily to these same clips.

Figure 14:
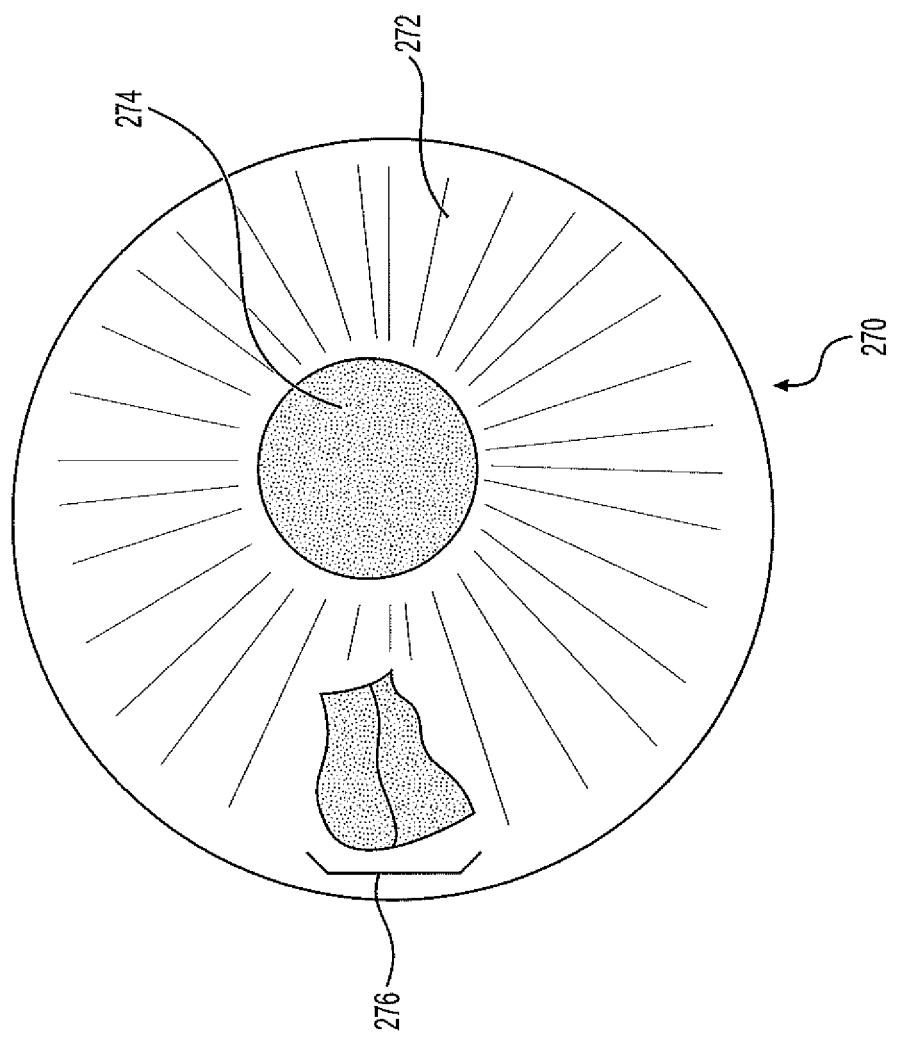
FIG. 14 is a top view of an eye with a defective iris.
Figure 15:
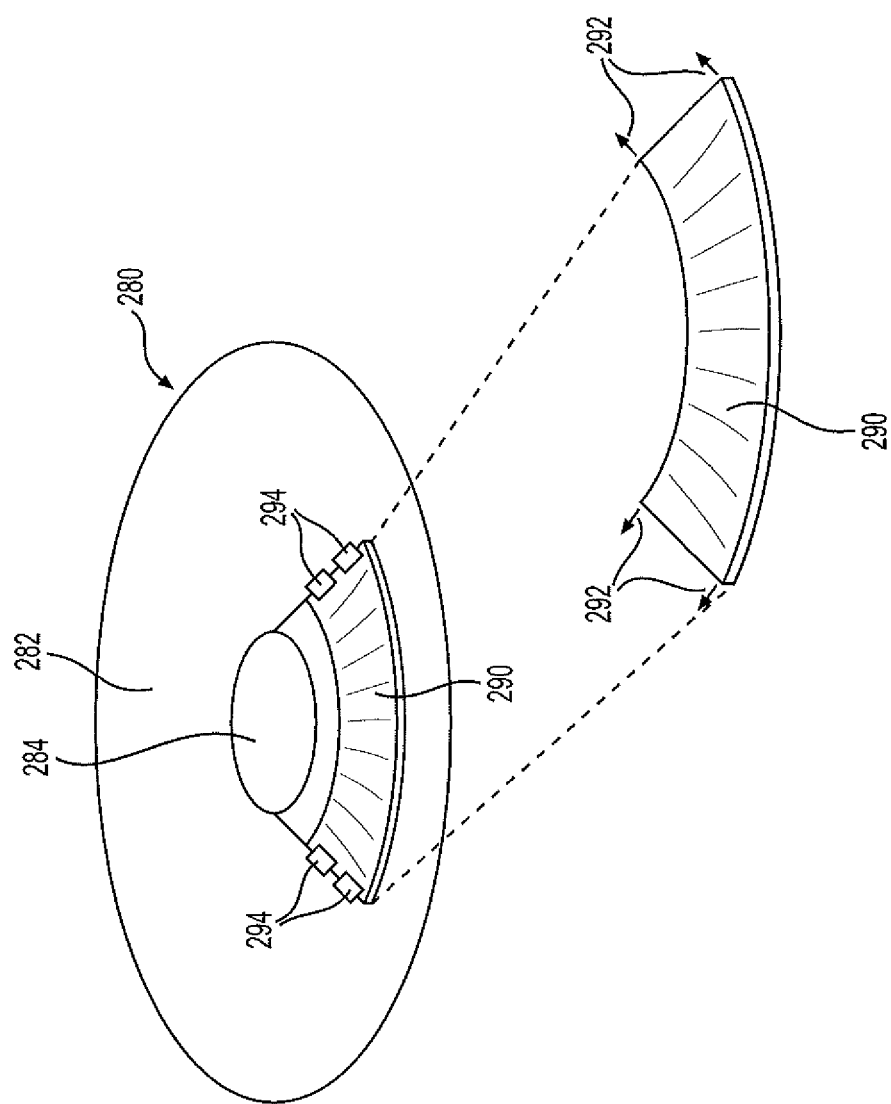
FIG. 15 is an exploded perspective view of a replacement scaffold clipped over a defective iris.

FIGS. 14 and 15 illustrate the use of clips to patch a damaged or defective iris. In FIG. 14, an eye 270 has an iris 272 and pupil 274. On the left side of eye 270 there is a portion of the iris 276 that is defective or missing or has no or reduced amount of pigment. As shown in FIG. 15, the eye 280 has an iris 282 and pupil 284. A scaffold patch 290 is a sheet of artificial or replacement iris. The scaffold 290 has attachment tubes 292 secured to the four corners of the scaffold. In use, the scaffold 290 is inserted inside eye 280, and using the attachment tubes 292 as tethers, the scaffold is secured to the iris 282 and over the flawed patch of iris using clips 294 as described herein.

Figure 16:
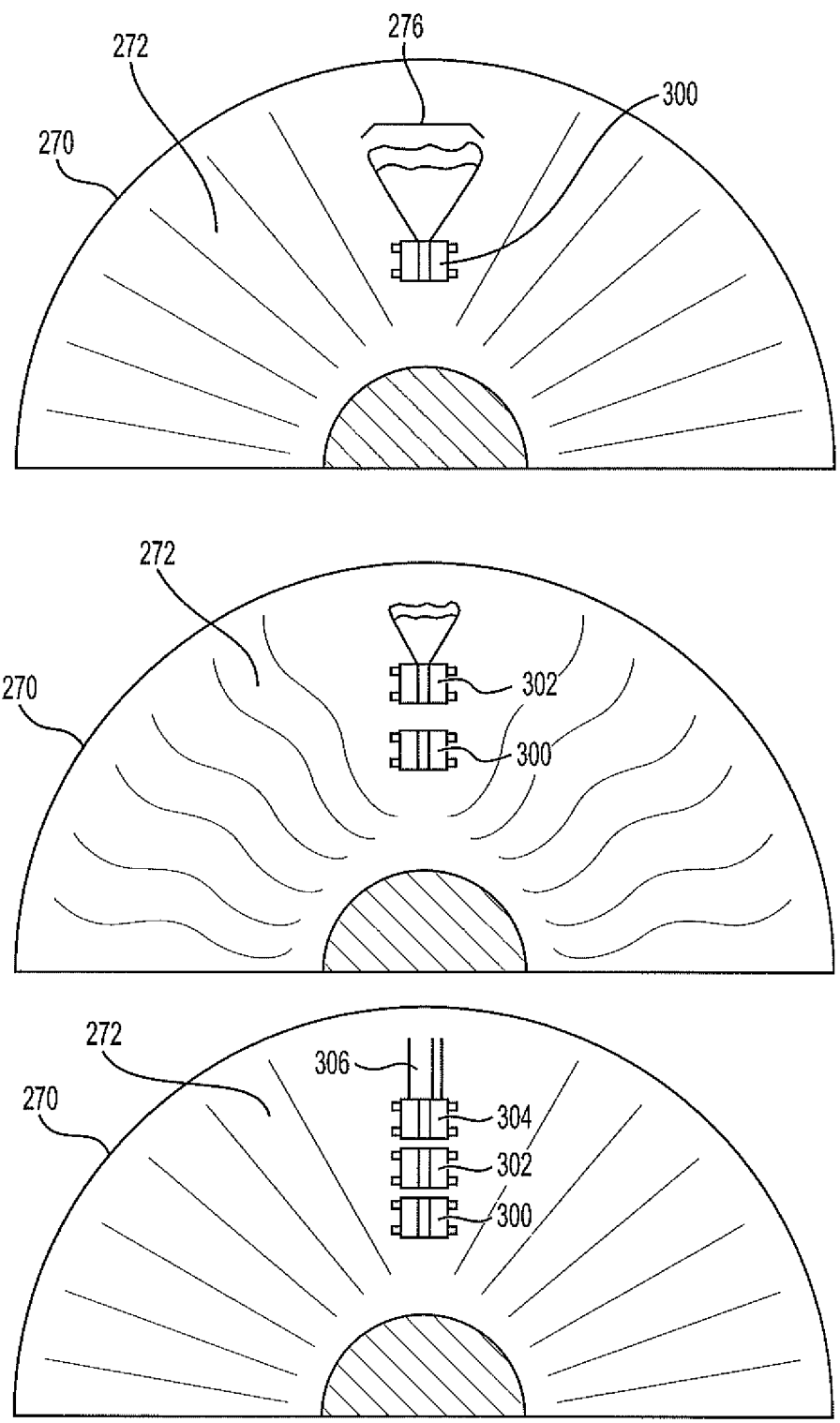
FIG. 16 is a series of three views illustrating how a defective iris may be repaired with examples of the iris clips described herein.

In FIG. 16, there is shown an alternative way to repair the iris defect 276 illustrated in FIG. 14. Starting at the top of FIG. 16, a first clip 300 is used to pull together the healthy tissue of iris 272 on each side of the defect 276. Second and third clips 302 and 304 are used to bring together the entire space of the defect 276 to create a new seam 306 in the eye that has healthy iris 272 all around the eye 270. Naturally, depending on the size of the defect and the size of the iris clips used, more or fewer than three clips may be used to join an iris together.

The clip may be clear or colored to match an iris pigment. In an eye with a pupil defect, the reconstruction of the iris can be accomplished by placing clips laterally to tense the iris into a round pupil of adequate size. These clips may be curved or straight. The clips may be strung together by a strand to allow for two or more clips to cerclage or dilate a pupil. Two curved clips interconnected with a circling band could be used to enlarge or reduce a pupil size. By this method an interconnector that is adjustable by advancing it through the clips would allow for adjustment of the ideal size desired.

Figure 17:
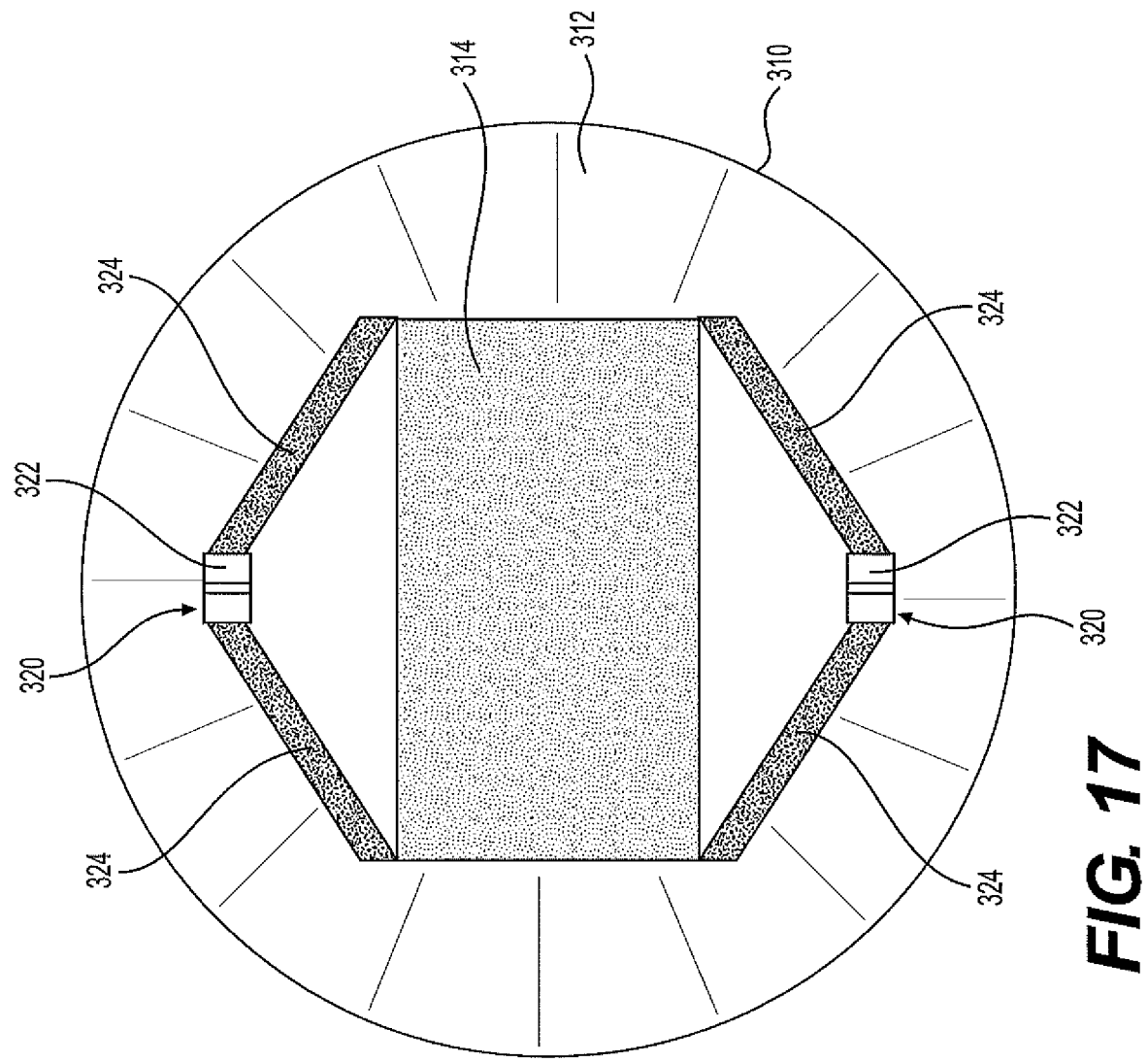
FIG. 17 is a top view of an example of an iris pupil expander.
Figure 18:
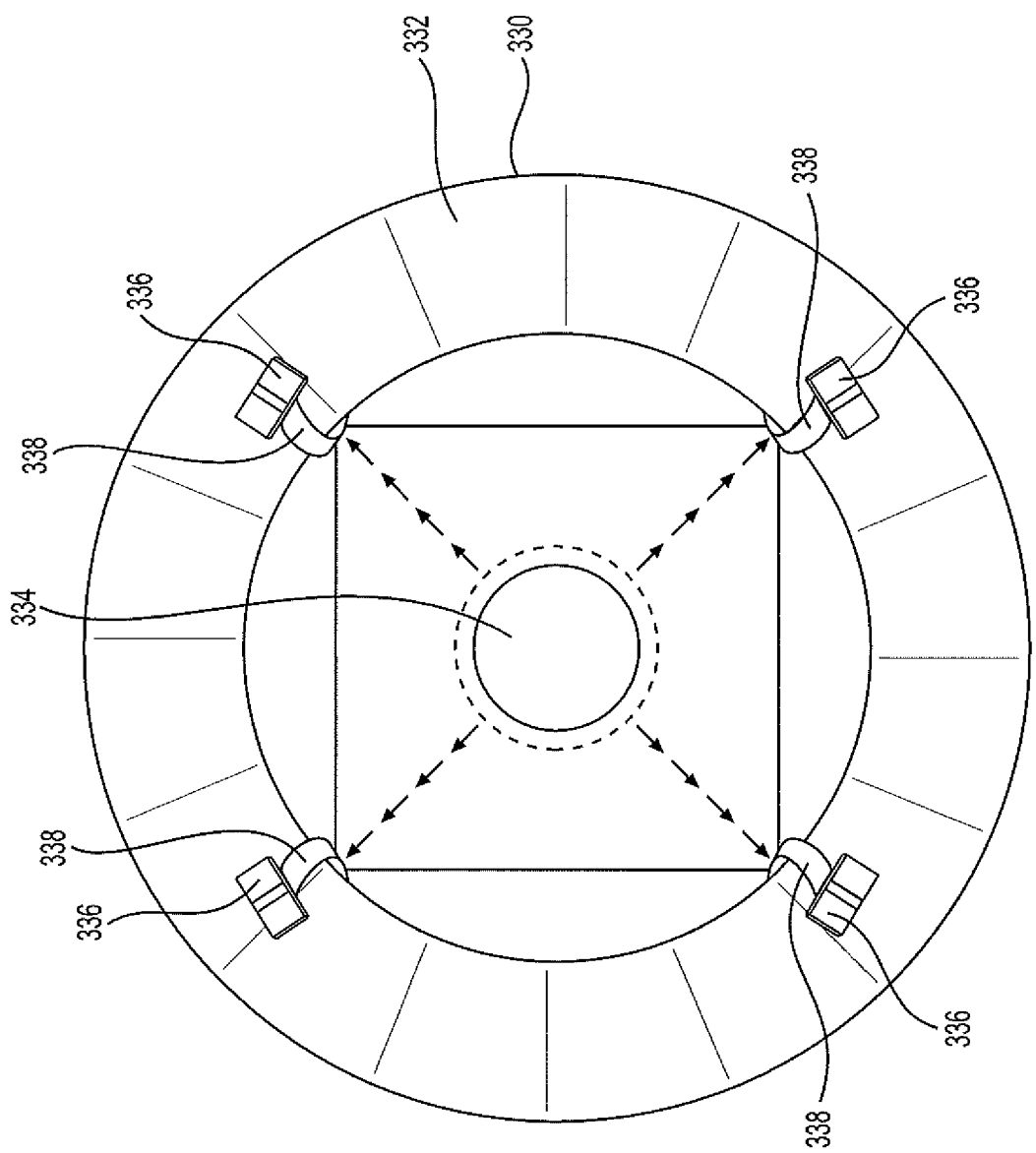
FIG. 18 is a top view of a second example of an iris pupil expander.
Figure 19:
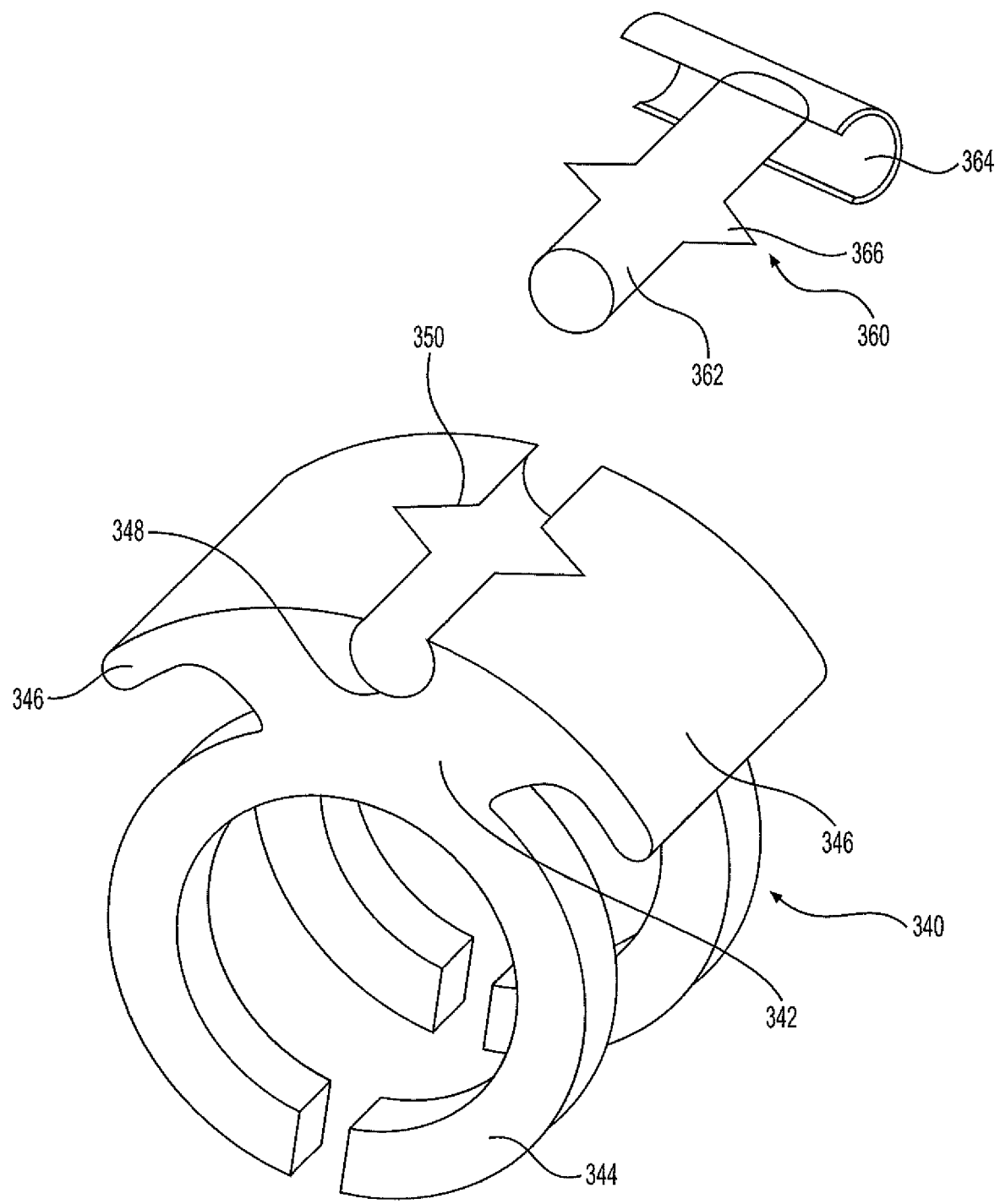
FIG. 19 is a perspective view of an example of an iris clip that may be used to expand an iris pupil.

In one example of pupil expansion, FIG. 17 illustrates an eye 310 with an iris 312 and pupil 314. A pair of clips 320 are show on the top and bottom of the iris 312. Each clip 320 has a central piece 322 and extensions 324. The central portion 322 of each clip 320 is secured to the body of the iris 312. The extensions 324 of the clips 320 are then clipped to the iris 312 to pull out the iris from the pupil to enlarge the opening of the pupil. In FIG. 18, an alternative method of pupil expansion is used. The eye 330 has an iris 332 and pupil 334. Clips 336 are secured to the middle or outside portion of an iris 332. Each clip 336 has a hook 338 secured to it. The hook 338 is used to capture the inside of the iris 332 and pull it out, thereby expanding the iris opening. FIG. 19 illustrates an example of the clip/hook combination discussed in FIG. 18. In FIG. 19, there is an iris clip 340 that includes a flexible body 342 and fasteners 344. The flexible body includes wings 346 and a central channel 348. The central channel 348 includes notches 350 in the longitudinal center of the channel 348. The iris hook 360 includes a tubular post 362 with extensions 366. At the end of the post 362 there is a semicircular portion 364 that will serve to hook and hold iris tissue. As shown in FIG. 18, the iris clips 340 would be fixed in the iris at approximately four corners around the iris. The iris hook 360, and specifically the semicircular portion 364, is used to gather and hold the inside edge of the iris and draw it out to the desired size of pupil in the middle of an eye.

Figure 20:
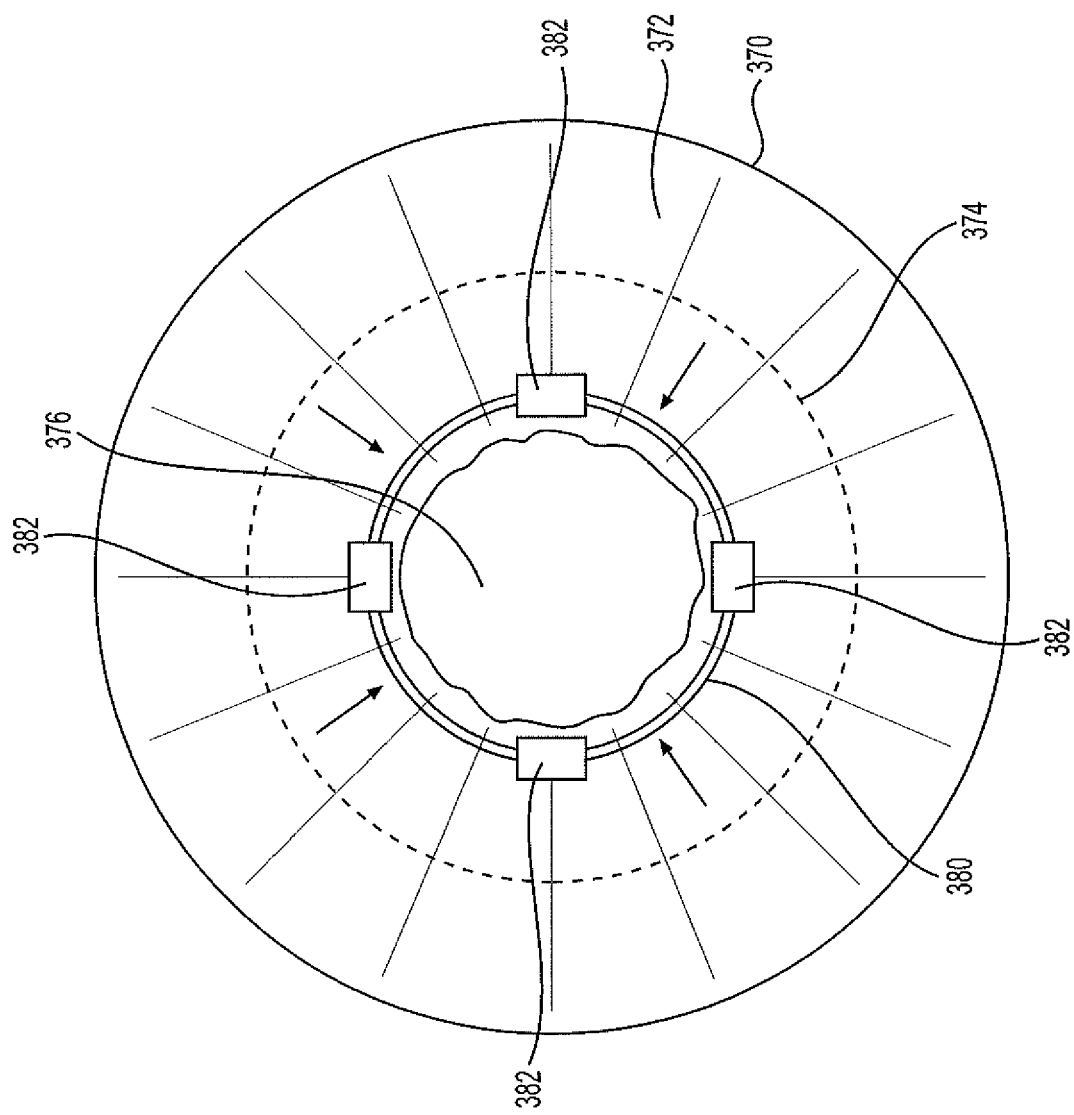
FIG. 20 is a top view of an example of a ring and clip combination used to shrink an iris pupil.

In another example, as shown in FIG. 20, an eye 370 has an iris 372 and pupil 376. The natural inside diameter 374 of the iris 372 is shown in dotted line. A selected ring 380 has four clips 382 attached to it. The ring 380 is selected for its specific diameter. The iris 372 is grabbed and pulled in and secured by the clips to the ring 380 to obtain the smaller inside diameter shown. In this way, the pupil is shrunk to a desired diameter based on the selection of the size of the ring 380.

Figure 21:
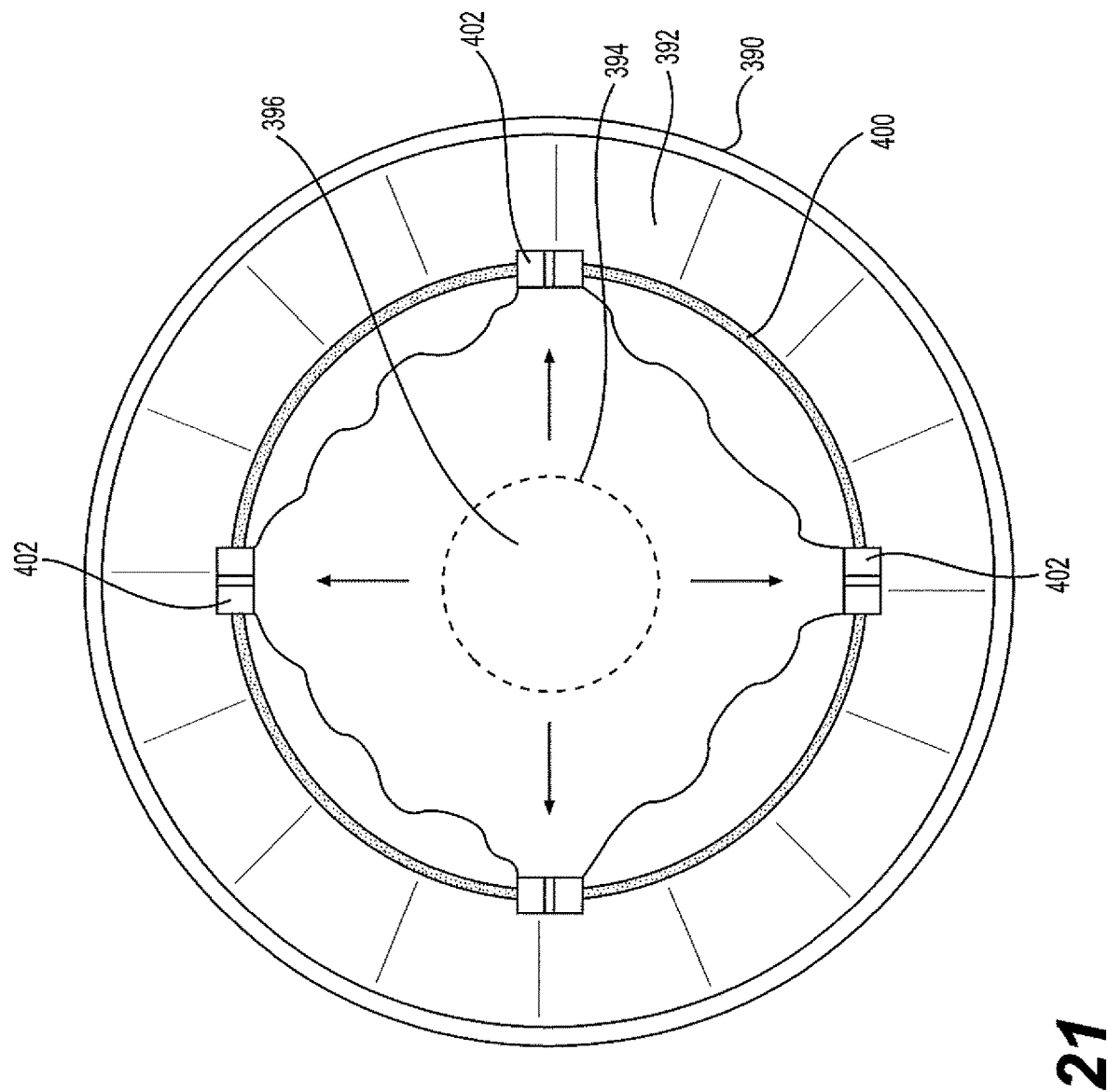
FIG. 21 is a top view of an example of a ring and clip combination used to expand an iris pupil.

In FIG. 21, an eye 390 has an iris 392 and pupil 396. The eye 390 has a natural inside diameter 394 shown in dotted lines. A selected ring 400 has four iris clips 402 secured to it. This ring 400 is selected for its diameter size. The clips 402 are secured to the iris tissue inside diameter and pulled outwardly to create a large pupil 396. Therefore, contrary to shrinking the pupil as shown in FIG. 20, the pupil 396 is grown by selecting a larger ring 400 in FIG. 21.

Figure 22:
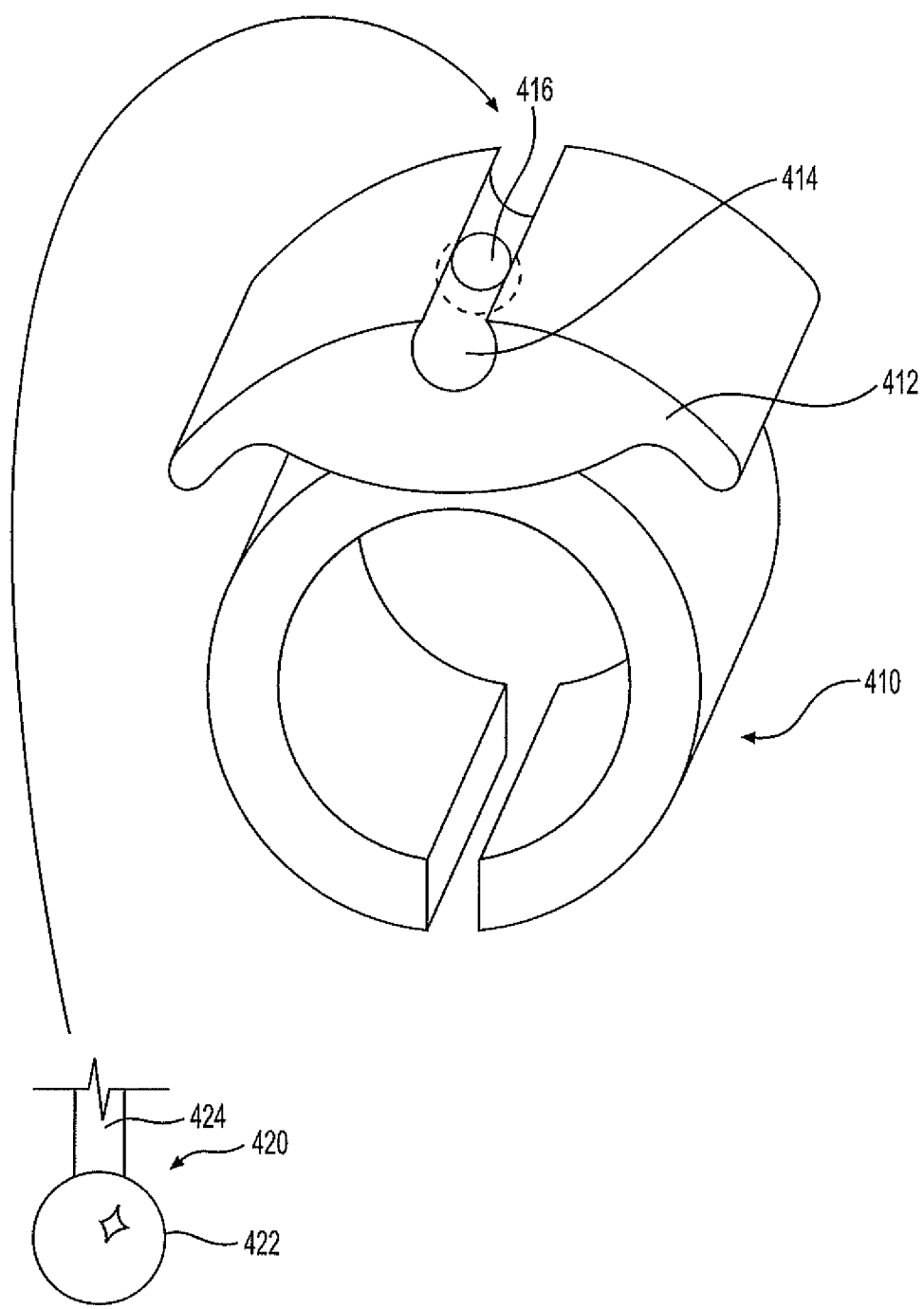
FIG. 22 is a perspective view of an iris clip with an example of a connector system.

In FIG. 19, the attachment system of a pupil expander hook 360 includes the post 362 inserted into channel 348 and secured there by a notch 350 and extension 366 means. In FIG. 22, an alternative attachment system is shown. The iris clip 410 has a flexible body 412 with a central channel 414. A round hole 416 is formed in a position on the inside length of the channel 414. A connector 420 includes a ball 422 and post 424 adapted and sized to be inserted into and held in the hole 416 of clip 410. This connector 420 may be used for connection to a ring or hook or some other intraocular appliance as a means of anchoring such item to an iris clip like clip 410.

A still further attachment system is shown in FIG. 23. Two iris clips 430 and 440 have flexible bodies 432 and 442 and fasteners 434 and 444. In each of clip 430 and 440, there are cross channels 436 and 438 and 446 and 448 respectively across the top of the flexible bodies 432 and 444 respectively. In this figure, a ring 450 is shown extending through channels 436 and 446 for instance in connection with the expansion or reduction of pupil dilation. Alternatively, the cross channels 438 and 448 could be used depending on how the clips 430 and 440 are deployed in the iris tissue. The use of cross channels can vary depending on the intended function of the clips. Also, the channels shown in FIG. 23 are shown in a perpendicular X-shape, but other on even more channels may be formed on different clip flexible bodies.

A common issue facing cataract surgery, "floppy iris," is often caused by alpha agonist drugs used for urinary flow improvement in the case of benign prostatic hypertrophy. In the case of floppy iris, the iris does not dilate well and is prone to sweeping out of the eye during surgery leading to pain and an iris defect under the incision. Currently in these cases the options are iris hooks which require making four incisions and hooking the iris to stretch it open into a square. An alternative method is a ring that is inserted into the anterior chamber and captures the edge of the pupil to stretch it open. The primary device in use is known as the Malyugin ring. The iris clip could be effectively used to clip the iris open quickly with less manipulation and less threat of creating an edge tear in the iris from the hooks or ring. These would be designed to capture more iris tissue with a curved clip. The mid iris zone would be the ideal place to put two or more clips to allow for adequate exposure of the lens or the retina for surgical access. The device is disinserted with a spreading tool. A micro hook approach can by coupling a clip to a small hook. In this method, the iris is hooked with a curved retractor and the clip is secured an adequate distance to gain exposure. Two to four clips could be used if the iris capture zone were elongated and curved. The iris requires minimal tension to gain retraction. These could be quickly secured and released. This method avoids multiple corneal incision to secure the hooks and would be gentler on the iris tissue which is friable and can be damaged or torn or come loose during surgery with a tiny hook. The Malyugin ring requires some skill to insert and disengage and will not give flexibility to the desired or needed dilation. This procedure is illustrated in one example in FIG. 21. A ring may secure the iris during a surgery and then removed upon completion of a procedure.

The clip could be made of absorbable polymers that could be used to provide postoperative antibiotic and or steroids at the conclusion of surgery. As devices are currently in development to allow this, the clip could be an adjunct to attach these pellets.

When an IOL has no capsular support or a capsule is missing, the Wurst IOL can be clipped onto the anterior or posterior iris to secure it. This is a "claw" design and gives two-point clipping to this unique lens. Other IOLs must be attached to the sclera by placing the haptic of the IOL into the sclera or by using sutures. Iris suturing of a three-piece IOL to the iris has been described but is technically difficult and time-consuming maneuver. Iris clips can be used to attach any lens to the iris. The method in its simplest form would be to hold the IOL behind the iris and place a clip over the haptic portion to the IOL through the iris. One or two clips per arm of the IOL would provide a method to place virtually any IOL including tonic IOLs and possibly multifocal IOLs. In an alternative method a clip may be placed over the haptic of the IOL and it could then be reverse captured through the iris using an endoscope for visualization or by counter pressure from above.

Technological devices can be securely placed onto the iris, using the clips described herein, like intraocular pressure measuring devices, drug delivery devices, stimulators, and possibly video systems. The pupil could be covered with a clipped lens or magnifying device using a ring that is clipped over the central iris. The lens could then be inserted into the ring. In a patient with macular loss a strong magnifier or telescope could be attached via this system. As the pupil constricts on accommodation, if a flexible lens were placed over the pupil, the clipping of an IOL over or under the pupil could allow it to thicken or thin providing magnification on looking at a close object via accommodation reflex.

Currently, in severe glaucoma, an Ahmed valve provides a release of pressure via a tube placed into the eye existing to the device that is under the conjunctiva. The clip could be used to secure the end of the tube which can sometimes lead to corneal loss from the free tip of the valve being unsecured.

Many new glaucoma devices could be iris clipped into the angle if this were available by design.

The size of the clip devices will vary by the intended purpose. The basic radial clip will have a length of less than 2 mm in general to allow for grasping and releasing, or alternatively a length of about 0.5-3 mm or about 1-2 mm. Larger devices, for example 3-10 mm, or alternatively 5-8 mm, would be used for pupil expansion or covering zones of iris loss. The clip device could be made to change color or to deliver meds using electromagnetic energy. The clip device may use nano pumps to deliver meds or to expand or contract to accommodate light. A light sensor can respond to light by expanding or contracting a clipped chamber which would cause the pupil to open and close. The device left in the eye could be made cosmetic if desired. This could include color, fluorescence and facets.

An insertion tool, as shown for instance in FIGS. 12 and 13, is used to place a clip inside a patient eye. In the pre insertion states, the clip devices are biased closed. The insertion tool must open the tension on the clip to gather iris tissue for capture. Gently sweeping the iris with a second tool to gather the desired amount is one tactic. The clips can be loaded on serially to allow for the next clip to be advanced for clipping immediately. The tool could gather the iris itself by grasping laterally before securing the clip with comb like extensions.

Retro illumination often best shows areas of thinning that may benefit from coverage or closure. As the iris strands may be covering the area of lost tissue without back illuminating the zone the defect that would allow light through may not be seen. A retro illumination fiber optic may be attached to the clip device directing light into the pupil. As blood vessels feed the iris tissue, the use of a fiber optic device or an infrared device to better visualize the areas of vascularization would assist in the precise placement of the clips to avoid ischemia. Retro illumination devices are currently used to identify veins for phlebotomy. Their application for iris manipulation would be a simple adaptation.

A clip could include a nano pump attached to it or integrally formed with it which could be activated by a light sensor. In one example, the nano pump would deliver aqueous solution to a bladder that could bring a circle of clips further apart or closer together. The expansion of the pupil or constriction could be left in place or be continuous by external control by the use of electromagnetic or Bluetooth like technology. A nano pump clip could alternatively be used to deliver medication to the anterior or by cannulation to the vitreous posterior medication to the eye. The nano pump can be directed by external electromagnetic or Bluetooth or other technology. The bladder to the device could be placed posterior to the iris to allow for a larger delivery over time.

The ability to secure devices into the eye by using the clipping attachment allows for countless applications including retinal stimulators using a video camera, a magnifying telescope that could be clipped over the pupil and controlled by Bluetooth to allow for larger and smaller magnification. An internal contact lens that clips over the iris or under the iris in the aphakic patient could be made to accommodate or steepen by iris movement or external control. As the device can be quickly removed and replaced by though a small incision, the devices could be replaced quickly and safely.

Current IOLs, like the Visian lens, are placed over the zonules and behind the iris and suffer for cataract and pigment dispersion even when perfectly sized. This system would allow for a more robust and featured device that is placed in the anterior chamber or clipped through the iris posteriorly. Like the Wurst lens it would clip over the pupil or uniquely clip through the iris posteriorly. But unlike this device the multiple clips make IOL design capable or using foldable and high index material that could be vaulted up from the pupil and could be capable of thinning or thickening centrally with iris movement or external control.

A ring with multiple clips could be used to expand a pupil by gathering iris tissue and attaching onto the ring. The advantage would be the pupil size could be the exact desired need and unlike suture could be easily reversed by unclipping. It would also stabilize the iris in cases of floppy iris syndrome. In the opposite case, a tonic pupil could be clipped to the desired size to reduce glare and provide a better cosmetic appearance. Half rings with a central iris hook and two clips could effectively dilate. A single clip with a half ring and two expansion hooks could dilate with only two areas of clipping. This enlargement and shrinking of a pupil are shown for instance in FIGS. 21 and 20 respectively.

The lens capsule is a delicate tissue that when it tears or develops a hole vitreous may come forward and the IOL will not be able to be placed within it. A clip could be used to close these tears or holes. This version of the clip would likely have a smooth or textured/serrated grasping surface to hold without penetrating the capsule. An IOL that has been placed inside the capsular "bag" could be clipped to the bag with overlapping clips that hold the IOL to the anterior capsule. This technique could also be used to secure an IOL in the precise position of centered, or angled in the case of astigmatism. IOL can shift after surgery and dramatically degrade the effectiveness of the IOL. By clipping the IOL into place it will assure that it maintains its proper position. The capsular bag is held in place by delicate strings called zonules. These can become weak and are often torn free leaving part of the capsular bag loose unattached. This can lead to lens tilt and decentration. Currently a ring can be placed into the bag to maintain the curvature and provide support in the area of "dehiscence". Over time these eyes are at risk of further lens tilt and decentration. Clips could solve this uncertainty. The capsular bag could be clipped to the Iris or to the zonular attachment area of the ciliary body. These clips could be placed under direct observation with an eye endoscope or by counter pressure to fold the iris into the clip.

The installation device consists of a thin arm with three rods in which fasteners are loaded. At the tip, several broad fasteners are placed, which are composed of material to allow them to be bent or sprung into the desired position onto the iris strands. See FIGS. 12 and 13.

The fasteners are designed to cause the least amount of trauma to the iris tissue while providing a secure grasp or the tissue. Ideally the tissue is gathered within the loops of a comb-like fastener without crushing the tissue. Crushing the tissue with a flat surface will lead to inflammation and tissue loss in the area of crush. The fasteners may have a single area of attachment or several areas of attachment separated to effect a broader area of closure. On the top surface of the flexible body is a C shaped groove or channel that will be used to snap in tubular attachments of devices. The flexible body channel may have a clip or notch to allow it to be secured and unsecured. The notch or groove may cross the top of the clip in lengthwise and crosswise fashion. In addition, at the cross point of the two C shaped grooves a ball cavity would further strengthen securing a device to the clip and would allow for minor rotation of a device attached. See, e.g., FIG. 22.

A 2-piece clip/fastener may have a hinge tensioned with a circular notching system to allow closure and reopening. The ability to attach a device to the iris fixated clip securely will benefit from the tension created by the center portion of the fastener where its own stiffness or the insert tension will hold the inserting groove in place so that the tube or ball inserted will not slide out of the groove but will remain in place after insertion.

The 2-piece clip/fastener may have a single of multiple areas of bunching and attachment to the iris fibers. Several fasteners may work in tandem to secure as an example, a ring, an iris replica or a aperture over the pupil. The 2 piece clip/fastener may have tension two densities of material to give the flexibility of opening and closing and the stiffness of attachment areas such as the attachment grooves and ball insert area or the comb area.

The fastener may have extensions to allow for an area of the iris lateral to the tensioner to be folded into the closure.

The fastener could attach to an aperture like device to allow for creating a pupil in a highly distorted pupil or to provide aperture effect for vision. This depth of focus aperture could be attached beyond the inner dilator muscle to allow for dilation.

The system may include "docking" features to allow for attachment of intraocular devices of all kinds onto several fasteners. The docking feature may be a loop, a notching system or ball system to allow for motion. The rotation of the lens to give astigmatic correction will be accomplished by a ring loop that allows for the IOL to slide around to its proper position from the external or internal clips. The clip would engage the ring and allow it to slide for rotation.

The fixation can be a small loop or slit that can be engaged. The loop spring may facilitate the dock.

The manipulator and fixation device may be loaded with a spreading tool that facilitate opening and closing of the fastener. These are opened from the use of an internally routed forward and reverse connections from the handpiece by which a finger of thumb may manipulate the tongs. See for instance FIG. 12. The inserter may have a series of fasteners that advance to the tongs after each one is attached to allow for the next fastener to be attached. An advancing system will reload the next fastener for closure onto the iris. The advancing mechanism may be manual or use a tensioning device within the application instrument.

The iris clips may have an attachment for securing secondary devices to the iris. These may include for example a drug delivery pellet or gel, a monitoring tool, like an intraocular pressure measuring device, a light sensor that allows for pupil dilation or constriction by stimulating the constrictor or dilator muscles, an iris replica to cover defects or alter eye appearance, or a video camera that could be magnetically charged to allow stimulation of a retinal visualization chip. The iris clips may be triggerable to allow for communication to an external source using radio frequency or bluetooth. The clips may be interconnected to allow for pupil dilation or closure. Two rounded clips with a stiff inter-connection could be used to increase or decrease the pupil size. Three or more clips interconnected could be used similarly. These could be used permanently or as a temporary method of dilating a poorly dilated or nonfunctioning iris.

Interconnected clips could be used to attach beyond a defect and scaffold over a defect an iris replica. The iris replica could be matched with an iris photo of the existing iris.

A clip could be used to attach an IOL to the anterior capsule in a case of posterior capsular loss. The haptic or arm of the IOL would be clipped through the capsule by wrapping the capsule over the aim or haptic then placing the clip over the arm to secure it. The haptic is the string or arm that is shown in a J like shape going away from the central circle that is the lens. The lens is 6 mm and the bag is sits in is 13 mm. so to keep the lens centered behind the pupil you need an arm or a stiff suture material. A securing sleeve could be attached to the arm of the IOL or haptic. This sleeve would lock into the clip to allow for a broad area of attachment to the capsule. An IOL could be designed for use with clips to allow for multiple areas of attachment either to the iris or to the capsule.

The gripping area may have serration or overlapping flat zones that are shallow or deep to grasp but not crush the iris or capsular tissue. The comb section of the clip may be of various lengths to accommodate a thinner or thicker iris or for folding over a haptic below the Iris. The haptic may be clipped from the inside out. A nano pump on the clip could be used to release medication into the anterior or posterior chamber. A cannula from the pump could be directed into the vitreous for retinal delivery. A nano pump connected to a bladder clipped near the pupil may be directed to narrow or expand the distance between clips providing a mobile pupil in an eye that is tonic.

The clips may be used to place a telescope or magnifying device over or behind the pupil.

The clips may be used to place a filter over the pupil to limit light. The filter may be photosensitive.

The clip may be one piece or multiple pieces that clip together to form a matrix over an area of defect.

The clip may intra lock with a locking mechanism on the top part of the clip. Iris that is thin near a defect could then be avoided by drawing thicker iris from a peripheral spot and drawing this together with an adjacent clip on the other side of the defect.

The clip gripping and bending element will act as a receptacle for a reverse clip that can attach devices to the clip. These could include rings, IOL attachment, devices such as drug delivery.

The clip could be used to clamp with a curved clamp onto the area of zonular attachment over the ciliary body. The IOL could then be clipped to the device to secure it in the effective lens position. This maneuver would be accomplished using an endoscope to visualize the area of attachment.

Other embodiments of the present invention will be apparent to those skilled in the art from consideration of the specification. It is intended that the specification and figures be considered as exemplary only, with a true scope and spirit of the invention being indicated by the following claims.

That which is claimed is:

1. An intraocular clip comprising
   a flexible body connected to a plurality of fasteners,
   wings connected to and extending outwardly from and on opposite sides of the flexible body;
   wherein the fasteners are configured on opposite sides of the body in an opposing relationship, and wherein the fasteners are biased to be engaging their respective opposing fasteners on the opposite sides of the body, however manipulation of the body moves the fasteners away from each other until the body is released and the fasteners bias toward each other,
   the fasteners have a proximal end joined to the body and a distal end on the opposite end of the fastener from the body, and the distal ends of the fasteners comprise footpads, and the footpads on opposing fasteners engage each other when the fasteners are biased in their closed positions.

2. An intraocular clip as described in claim 1, wherein the flexible body and plurality of fasteners are a single unitary piece.

3. An intraocular clip as described in claim 1, wherein the fasteners are a plurality of opposing comb extensions.

4. An intraocular clip as described in claim 1, wherein the clip defines a length, and the length of the clip is between 0.5 and 5 mm.

5. An intraocular clip as described in claim 1, wherein the clip defines a length, and the length of the clip is between 1 and 2 mm.

6. An intraocular clip as described in claim 1, wherein the footpads have a flat face.

7. An intraocular clip as described in claim 1, wherein the footpads have a textured face.

8. An intraocular clip as described in claim 1, wherein the footpads have a pointed face.

9. An intraocular clip as described in claim 1, further comprising a spring attached to the body to bias the body to urge the fasteners together in a closed position.

10. An intraocular clip comprising
a flexible body connected to a plurality of fasteners,
wherein the fasteners are configured on opposite sides of the body in an opposing relationship, and wherein the fasteners are biased to be engaging their respective opposing fasteners on the opposite sides of the body, however manipulation of the body moves the fasteners away from each other until the body is released and the fasteners bias toward each other,
the fasteners have a proximal end joined to the body and a distal end on the opposite end of the fastener from the body, and
the distal ends of the fasteners comprise fingers that are overlapping when the fingers are biased in their closed positions.

11. An intraocular clip as described in claim 10, further comprising a spring attached to the body to bias the body to urge the fasteners together in a closed position.

* * * * *